(12) United States Patent
Brostrom et al.

(10) Patent No.: US 7,767,850 B2
(45) Date of Patent: Aug. 3, 2010

(54) S-[2-[(1-IMINOETHY)AMINO]ETHYL]-2-METHYL-L-CYSTEINE MALEATE HYDROCHLORIDE CRYSTALLINE SALT

(75) Inventors: Lyle Brostrom, Lincolnshire, IL (US); Ann Czyzewski, Grayslake, IL (US); Vahid Zia, San Francisco, CA (US); Ahmad Sheikh, Dearfield, IL (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 12/315,744

(22) Filed: Dec. 5, 2008

(65) Prior Publication Data
US 2009/0215891 A1 Aug. 27, 2009

Related U.S. Application Data

(63) Continuation of application No. 10/797,462, filed on Mar. 10, 2004, now abandoned.

(60) Provisional application No. 60/453,496, filed on Mar. 11, 2003.

(51) Int. Cl.
*C07C 323/25* (2006.01)
(52) U.S. Cl. ..................................... 562/557
(58) Field of Classification Search .................. None
See application file for complete search history.

(56) References Cited

U.S. PATENT DOCUMENTS 6,403,830 B2    6/2002  Webber et al.

OTHER PUBLICATIONS

McInnis et al.; Production of Nitric Oxide in the Synovial Membrane of Theumatoid and Osteoarthritis Patients; J Exp Med; 184; 1519; 1996.
Lundberg et al; Greatly Increased luminal nitric oxide in ulcerative colitis; Lancet; vol. 344; p. 1673; Dec. 17, 1994.
Hamid et al; Induction of nitric oxide synthase in asthma; Lancet; vol. 342; p. 1510; Dec. 1993.
McMasters, Chem 2O06 Laboratory 1997, Expt. 1, Part B. Recrystallization and Melting Point Determinations.

*Primary Examiner*—Paul A Zucker
(74) *Attorney, Agent, or Firm*—A. David Joran; Philip B. Polster, II

(57) ABSTRACT

A novel mixed salt of S-[2-[(1-Iminoethyl)amino]ethyl]-2-methyl-L-cysteine is disclosed. The novel mixed salt, S-[2-[(1-Iminoethyl)amino]ethyl]-2-methyl-L-cysteine maleate hydrochloride, may be produced to form crystals that may be arranged as generally orderly packed agglomerates, which are particularly useful in making pharmaceutical compositions. Such pharmaceutical compositions are also described, as well as methods to make crystalline S-[2-[(1-Iminoethyl)amino]ethyl]-2-methyl-L-cysteine maleate hydrochloride, and methods of treating conditions characterized by an overexpression on nitric oxide from the inducible isoform of nitric oxide synthase using the S-[2-[(1-Iminoethyl)amino]ethyl]-2-methyl-L-cysteine maleate hydrochloride.

10 Claims, 13 Drawing Sheets
(6 of 13 Drawing Sheet(s) Filed in Color)

S-[2-[(1-IMINOETHY)AMINO]ETHYL]-2-METHYL-L-CYSTEINE MALEATE HYDROCHLORIDE CRYSTALLINE SALT

Priority is claimed from U.S. Provisional Application Ser. No. 60/453,496, filed Mar. 11, 2003 incorporated herein by reference.

FIELD OF THE INVENTION

The present invention comprises a novel compound useful in the treatment of disease, and more particularly a novel salt of S-[2-[(1-Iminoethyl)amino]ethyl]-2-methyl-L-cysteine, and even more particularly a novel crystalline S-[2-[(1-Iminoethyl)amino]ethyl]-2-methyl-L-cysteine maleate hydrochloride, and pharmaceutical compositions thereof, for the treatment of conditions involving an inappropriate expression of nitric oxide from the inducible isoform of nitric oxide synthase.

S-[2-[(1-Iminoethyl)amino]ethyl]-2-methyl-L-cysteine is described and claimed in commonly assigned U.S. Pat. No. 6,403,830, herein incorporated by reference.

BACKGROUND OF THE INVENTION

Nitric oxide (NO) is a bioactive free radical gas produced by any one of several isoforms of the enzyme nitric oxide synthase (NOS). The physiological activity of what was later identified as NO was initially discovered in the early 1980's when it was found that vascular relaxation caused by acetylcholine is dependent on the presence of the vascular endothelium. The factor derived from the endothelium, then called endothelium-derived relaxing factor (EDRF), that mediates such vascular relaxation is now known to be NO that is generated in the vascular endothelium by one isoform of NOS. The activity of NO as a vasodilator has been known for well over 100 years. In addition, NO is the active species derived from known nitrovasodilators including amylnitrite, and glyceryltrinitrate. Nitric oxide is also an endogenous stimulator of soluble guanylate cyclase (cGMP), and thus stimulates cGMP production. When NOS is inhibited by N-monomethylarginine (L-NMMA), cGMP formation is completely prevented. In addition to endothelium-dependent relaxation, NO is known to be involved in a number of biological actions including cytotoxicity of phagocytic cells and cell-to-cell communication in the central nervous system.

The identification of EDRF as NO coincided with the discovery of a biochemical pathway by which NO is synthesized from the amino acid L-arginine by the enzyme NO synthase. There are at least three types of NO synthase as follows:

(i) a constitutive, Ca++/calmodulin dependent enzyme, located in the brain, that releases NO in response to receptor or physical stimulation;

(ii) a Ca++ independent enzyme, a 130 kD protein, which is induced after activation of vascular smooth muscle, macrophages, endothelial cells, and a number of other cells by endotoxin and cytokines; and (iii) a constitutive, Ca++/calmodulin dependent enzyme, located in the endothelium, that releases NO in response to receptor or physical stimulation.

Once expressed, inducible nitric oxide synthase (hereinafter "iNOS") generates NO continuously for long periods. Clinical studies have shown that NO production and iNOS expression are increased in a variety of chronic inflammatory diseases, such as rheumatoid and osteoarthritis (see, e.g., McInnes I. B. et al., *J. Exp. Med.* 184:1519 (1996)), inflammatory bowel disease (see, e.g., Lundberg J. O. N. et al., *Lancet* 344:1673, (1994)), and asthma (see, e.g., Hamid, Q. et al., *Lancet* 342:1510 (1993)), and iNOS is implicated as a major pathological factor in these chronic inflammatory diseases.

Thus, inhibition of excessive NO production by iNOS is likely to be anti-inflammatory. However, since the production of NO from eNOS and nNOS is involved in normal physiology, it would be desirable for any NOS inhibitor that is used for treating inflammation be selective for iNOS, so that normal physiological modulation of blood pressure by eNOS-generated NO, and non-adrenergic, non-cholinergic neuronal transmission by nNOS-generated NO would remain unaffected.

With all pharmaceutical compounds and compositions, the chemical and physical stability of a drug compound is important in the commercial development of that drug substance. Such stability includes the stability at ambient conditions, especially to moisture and under storage conditions. Elevated stability at different conditions of storage is needed to predict the different possible storage conditions during the lifetime of a commercial product. A stable drug avoids the use of special storage conditions as well as frequent inventory replacement. A drug compound must also be stable during the manufacturing process which often requires milling of the drug to achieve drug material with uniform particle size and surface area. Unstable materials often undergo polymorphic changes. Therefore, any modification of a drug substance which enhances its stability profile provides a meaningful benefit over less stable substances.

Several inhibitors of iNOS have been described, such as, for example, S-[2-[(1-iminoethyl)amino]ethyl]-2-methyl-L-cysteine, which is described and claimed in commonly assigned U.S. Pat. No. 6,403,830. That compound, however, is an amorphous solid. It would be desirable, therefore, to provide a crystalline solid form of an iNOS inhibitor such as S-[2-[(1-Iminoethyl)amino]ethyl]-2-methyl-L-cysteine.

BRIEF DESCRIPTION OF THE DRAWINGS

The patent or application file contains at least one drawing executed in color. Copies of this patent or application publication with color drawing(s) will be provided by the Office upon request and payment of the necessary fee.

FIG. 7 are two SEM pictures of the randomly packed agglomerates of crystalline S-[2-[(1-Iminoethyl)amino]ethyl]-2-methyl-L-cysteine maleate hydrochloride obtained from Example 9, FIG. 7A shows the generally random shape of the agglomerates, while

FIG. 9 shows two SEM pictures of the orderly packed agglomerates of crystalline S-[2-[(1-Iminoethyl)amino]ethyl]-2-methyl-L-cysteine maleate hydrochloride made through in-situ seeded QESD crystallization process and obtained from Example 23, FIG. 9A shows the generally cylindrical shape, while

SUMMARY OF THE INVENTION

Figure 1:
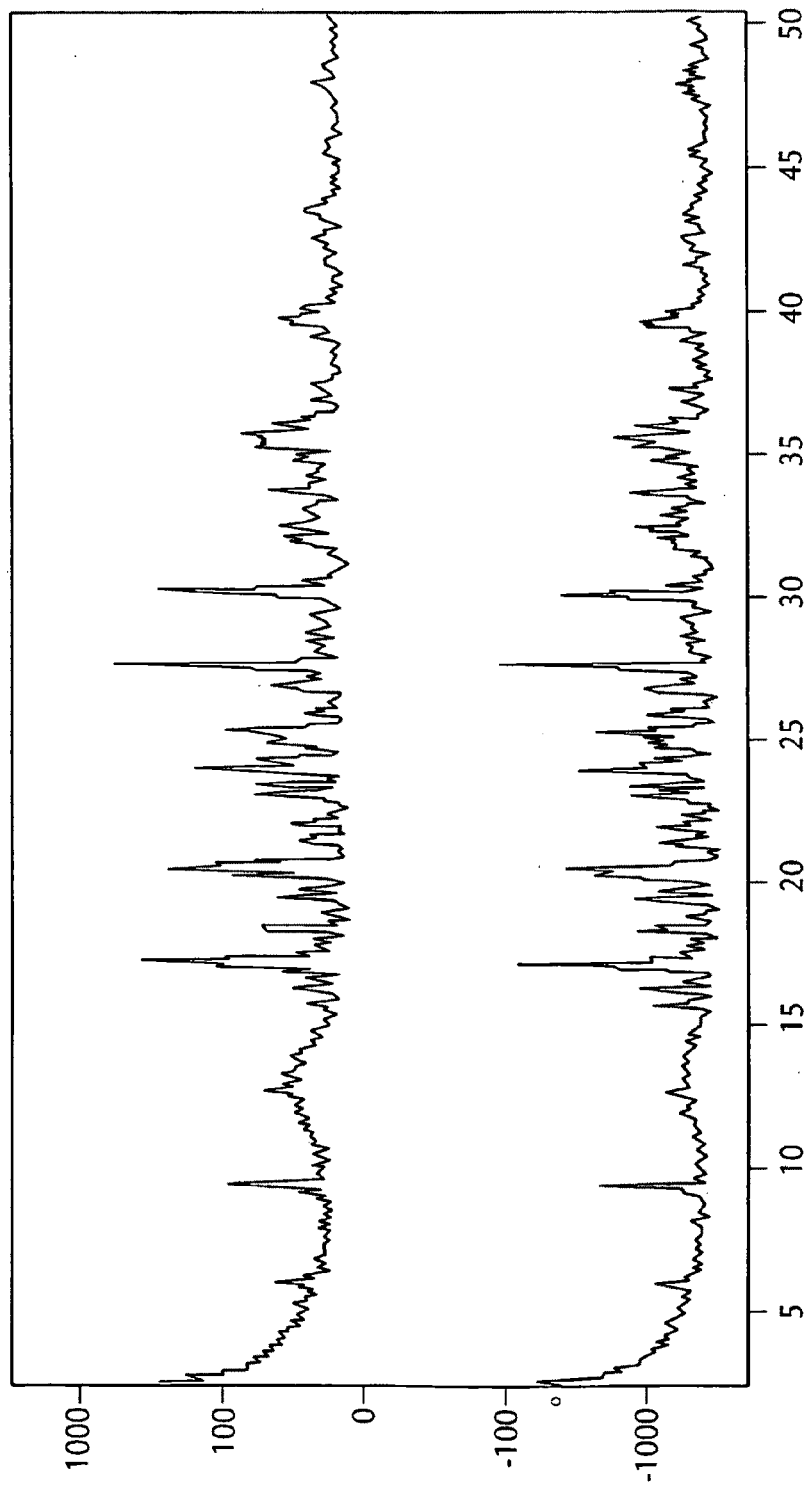
FIG. 1 shows a powder X-ray diffraction pattern of crystalline S-[2-[(1-Iminoethyl)amino]ethyl]-2-methyl-L-cysteine maleate hydrochloride obtained from Example 9 (top pattern) and Example 20 (bottom pattern)

The present invention is directed to a novel crystalline salt form of S-[2-[(1-Iminoethyl)amino]ethyl]-2-methyl-L-cysteine, pharmaceutical compositions, four mechanistically different novel crystallization process designs to tailor bulk physical properties during the preparation of the novel salt compound, a process for preparing pharmaceutical compositions, and methods of using said novel mixed crystalline salt compound and compositions for inhibiting or modulating nitric oxide synthesis in a subject in need of such inhibition or modulation by administering a salt of a compound which preferentially inhibits or modulates the inducible isoform of nitric oxide synthase over the constitutive isoforms of nitric oxide synthase. The present salt compound possesses useful nitric oxide synthase inhibiting activity, and is expected to be useful in the treatment or prophylaxis of a disease or condition in which the synthesis or oversynthesis of nitric oxide forms a contributory part.

Stoichiometrically, the novel salt is two molecules of S-[2-[(1-Iminoethyl)amino]ethyl]-2-methyl-L-cysteine with one molecule of maleic acid and one molecule of hydrochloride.

The novel crystalline mixed salt is characterized by some or all of the following physical measurements: elemental analysis (such as by combustion analysis), melting point and heat of fusion (differential scanning calorimetry and thermogravimetric analysis), refractive indices (polarized light microscopy), x-ray powder diffraction pattern, Raman spectroscopy and moisture sorption (for example, DVS moisture balance).

The present novel salt can be used to treat diseases involving cartilage degeneration, which takes place in certain conditions such as arthritis. Accordingly, conditions in which there is an advantage in inhibiting NO production from L-arginine include arthritic conditions such as rheumatoid arthritis, osteoarthritis, gouty arthritis, juvenile arthritis, septic arthritis, spondyloarthritis, acute rheumatic arthritis, enteropathic arthritis, neuropathic arthritis, and pyogenic arthritis. In addition, NO-induced depression of chondrocyte respiration could modulate matrix loss- and secondary cartilage mineralization in arthritis, in particular osteoarthritis.

Other conditions for which the present mixed salt may be useful include chronic or inflammatory bowel disease, cardiovascular ischemia, diabetes, congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia, cerebral ischemia, thrombotic stroke, global ischemia (secondary to cardiac arrest), multiple sclerosis and other central nervous system disorders mediated by NO, for example Parkinson's disease and Alzheimer's disease. Further neurodegenerative disorders in which NO inhibition may be useful include nerve degeneration and/or nerve necrosis in disorders such as hypoxia, hypoglycemia, epilepsy, and in external wounds (such as spinal cord and head injury), hyperbaric oxygen convulsions and toxicity, dementia e.g. presenile dementia, and AIDS-related dementia, Sydenham's chorea, Huntington's disease, Amyotrophic Lateral Sclerosis, Korsakoff's disease, imbecility relating to a cerebral vessel disorder, sleeping disorders, schizophrenia, depression, depression or other symptoms associated with Premenstrual Syndrome (PMS), anxiety and septic shock.

The present mixed salt may also be used where nitric oxide inhibition may also play a role in the treatment, such as pain including somatogenic (either nociceptive or neuropathic), both acute and chronic. The present mixed salt could be used in any situation that a common NSAID or opioid analgesic would traditionally be administered.

Still, other disorders that may be treated by inhibiting NO production with the present mixed salt include opiate tolerance in patients needing protracted opiate analgesics, and benzodiazepine tolerance in patients taking benzodiazepines, and other addictive behavior, for example, nicotine and eating disorders. The present mixed salt may also be useful as anti-bacterial agents.

Further conditions in which the present mixed salt may be used to inhibit NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy.

The present mixed salt may also be useful in the treatment of ocular conditions (such as ocular hypertension retinitis uveitis), systemic lupus erythematosis (SLE), glomerulonephritis, restenosis, inflammatory sequelae of viral infections, acute respiratory distress syndrome (ARDS), oxidant-induced lung injury, IL2 therapy such as in a cancer patient, cachexia, immunosuppression such as in transplant therapy, disorders of gastrointestinal motility, sunburn, eczema, psoriasis, gingivitis, pancreatitis, damage to the gastrointestinal tract resulting from infections, cystic fibrosis, treatment to a dysfunctional immune system such as an adjuvant to short term immunosuppression in organ transplant therapy, induction, of labor, adenomatous polyposis, controlling tumor growth, chemotherapy, chemoprevention and bronchitis.

The present invention is also directed to pharmaceutical compositions for the treatment of pain, asthma and other airway disorders, cancer, arthritis, ocular disorders including retinopathies and glaucoma, inflammation related disorders including irritable bowel syndrome, and other disorders in which an excessive production of nitric oxide plays a role, which comprises a therapeutically effective amount of crystalline S-[2-[(1-Iminoethyl)amino]ethyl]-2-methyl-L-cysteine maleate hydrochloride together with a pharmaceutically acceptable carrier, diluent or vehicle.

Besides being useful for human treatment, this form is also useful for veterinary treatment of companion animals, exotic animals and farm animals, including mammals, rodents, and the like. More preferred animals include horses, dogs, and cats.

DETAILED DESCRIPTION OF THE INVENTION

Definitions

The terms "treat," "treating" and "treatment," as used herein includes prophylactic, palliative treatment, or restorative treatment.

The term "effective amount" means a dose conducive to treatment. An effective amount may be administered in a single dose, or in divided doses over a period of time.

The term "ACN" means acetonitrile.

The term "amorphous" as applied to S-[2-[(1-Iminoethyl) amino]ethyl]-2-methyl-L-cysteine herein refers to a solid state wherein the S-[2-[(1-Iminoethyl)amino]ethyl]-2-methyl-L-cysteine molecules are present in a disordered arrangement and do not form a distinguishable crystal lattice or unit cell. When subjected to X-ray powder diffraction, amorphous S-[2-[(1-Iminoethyl)amino]ethyl]-2-methyl-L-cysteine does not produce any characteristic crystalline peaks.

The term "crystalline form" as applied to S-[2-[(1-Iminoethyl)amino]ethyl]-2-methyl-L-cysteine herein refers to a solid form wherein the S-[2-[(1-Iminoethyl)amino] ethyl]-2-methyl-L-cysteine molecules are arranged to form a distinguishable crystal lattice (i) comprising distinguishable unit cells, and (ii) yielding diffraction peaks when subjected to X-ray radiation.

The terms "S-[2-[(1-Iminoethyl)amino]ethyl]-2-methyl-L-cysteine maleate Form I," S-[2-[(1-Iminoethyl)amino] ethyl]-2-methyl-L-cysteine Form I" and "Form I" all mean S-[2-[(1-Iminoethyl)amino]ethyl]-2-methyl-L-cysteine maleate crystalline salt Form I, as more fully described in copending U.S. Application Ser. No. 60/453,796, incorporated herein by reference in its entirety.

The terms "S-[2-[(1-Iminoethyl)amino]ethyl]-2-methyl-L-cysteine maleate Form II," S-[2-[(1-Iminoethyl)amino] ethyl]-2-methyl-L-cysteine Form II" and "Form II" all mean S-[2-[(1-Iminoethyl)amino]ethyl]-2-methyl-L-cysteine maleate crystalline salt Form H, as more fully described in copending U.S. Application Ser. No. 60/453,782, incorporated herein by reference in its entirety.

The terms "S-[2-[(1-Iminoethyl)amino]ethyl]-2-methyl-L-cysteine maleate hydrochloride," crystalline S-[2-[(1-Iminoethyl)amino]ethyl]-2-methyl-L-cysteine maleate hydrochloride," and "mixed salt" all refer to the crystalline form of S-[2-[(1-Iminoethyl)amino]ethyl]-2-methyl-L-cysteine maleate hydrochloride, having stoichiometrically one mole of S-[2-[(1-Iminoethyl)amino]ethyl]-2-methyl-L-cysteine for 0.5 moles of maleate and 0.5 moles of HCl, as more fully described herein.

The term "crystallization" as used herein can refer to crystallization and/or recrystallization depending upon the applicable circumstances relating to preparation of S-[2-[(1-Iminoethyl)amino]ethyl]-2-methyl-L-cysteine starting material.

The term "API," as used herein, means active pharmaceutical ingredient.

The term "bis," as used herein, means N,N'-Methylene-bis-acrylamide

The term "DI water," as used herein, means deionized water.

The term "DMF," as used herein, means N,N-dimethylformamide.

The term "D/W/A" refers to a ternary solvent system of N,N-dimethylformamide (DMF), water and acetonitrile.

The term "S-[2-[(1-Iminoethyl)amino]ethyl]-2-methyl-L-cysteine drug substance" as used herein means S-[2-[(1-Iminoethyl)amino]ethyl]-2-methyl-L-cysteine per se as qualified by the context in which the term is used, and can refer to unformulated S-[2-[(1-Iminoethyl)amino]ethyl]-2-methyl-L-cysteine or to S-[2-[(1-Iminoethyl)amino]ethyl]-2-methyl-L-cysteine present as an ingredient of a pharmaceutical composition.

The term "DSC" means differential scanning calorimetry.

The term "$\Delta HR_{fus}$" or "$\Delta H$ fus" means the enthalpy of fusion of a substance, and refers to the energy (measured in kilojoules (Kj)) required to melt one gram of the substance at its melting point temperature.

The term "HPLC" means high pressure liquid chromatography.

The term "IR" means infrared.

The term "kN" means kilonewtons.

The term "kP" means kiloponds.

The term "$\rho$," or rho, as used herein, refers to density.

The term "$\rho_b$" means bulk density.

The term "$\rho_t$" means tapped density.

The term "CI" means Compressibility Index, as defined by the formula:

$$CI = 1 - \frac{\rho_b}{\rho_t}$$

The term "NMR" means nuclear magnetic resonance, and may apply to nuclear magnetic resonance spectroscopy.

The term "ml" means milliliters.

The term "mg" means milligrams.

The term "g" means grams.

The term "kg" means kilograms

The term "µg" means micrograms

The term "µl" means microliters.

The term "min" means minutes.

The term "MW" means molecular weight.

The term "nucleation," as used herein, means the formation of crystals in a solution.

The term "Purity" as used herein, unless otherwise qualified, means the chemical purity of crystalline S-[2-[(1-Iminoethyl)amino]ethyl]-2-methyl-L-cysteine maleate hydrochloride according to conventional HPLC assay.

The term "PXRD" means powder X-ray diffraction.

The term "rpm" means revolutions per minute.

The term "seeding," as used herein, means the addition of crystals to a crystallization system, for the purpose of initiating or enhancing nucleation or acting as substrate for further crystallization.

The term "agglomerates", generally refers to random or orderly packing of individual crystals in units that are not readily destroyed during energetically mild operations such as transfer of solids.

The term "SEM" means scanning electron microscopy.

The term "TGA" means thermogravimetric analysis.

The term "Tm" means melting temperature.

The term "zwitterion" or "ZW" means a molecule that carries both a positive and negative charge. The term "free zwitterion" means a zwitterion such that the net charge of the molecule is zero. Unless otherwise indicated, the term "zwitterion" and "ZW," as used herein, means S-[2-[(1-Iminoethyl)amino]ethyl]-2-methyl-L-cysteine zwitterion.

S-[2-[(1-Iminoethyl)amino]ethyl]-2-methyl-L-cysteine maleate hydrochloride crystalline salt will be useful for treating, among other things, inflammation in a subject, or for treating other nitric oxide synthase-mediated disorders, such as, as an analgesic in the treatment of pain and headaches, or as an antipyretic for the treatment of fever. For example, S-[2-[(1-Iminoethyl)amino]ethyl]-2-methyl-L-cysteine maleate hydrochloride crystalline salt will be useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis. Conditions in which the S-[2-[(1-Iminoethyl)amino]ethyl]-2-methyl-L-cysteine maleate hydrochloride crystalline salt will provide an advantage in inhibiting NO production from L-arginine include arthritic conditions.

S-[2-[(1-Iminoethyl)amino]ethyl]-2-methyl-L-cysteine maleate hydrochloride crystalline salt will be further useful in the treatment of asthma, bronchitis, menstrual cramps (e.g., dysmenorrhea), premature labor, tendinitis, bursitis, skin-related conditions such as psoriasis, eczema, burns, sunburn, dermatitis, pancreatitis, hepatitis, and from post-operative inflammation including from ophthalmic surgery such as cataract surgery and refractive surgery. S-[2-[(1-Iminoethyl)amino]ethyl]-2-methyl-L-cysteine maleate hydrochloride crystalline salt also would be useful to treat gastrointestinal conditions such as inflammatory bowel disease, Crohn's disease, gastritis, irritable bowel syndrome and ulcerative colitis.

S-[2-[(1-Iminoethyl)amino]ethyl]-2-methyl-L-cysteine maleate hydrochloride crystalline salt would be useful for the prevention or treatment of cancer, such as colorectal cancer, and cancer of the breast, lung, prostate, bladder, cervix and skin. S-[2-[(1-Iminoethyl)amino]ethyl]-2-methyl-L-cysteine maleate hydrochloride crystalline salt of the invention would be useful in treating inflammation and tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The S-[2-[(1-Iminoethyl)amino]ethyl]-2-methyl-L-cysteine maleate hydrochloride crystalline salt would also be useful in the treatment of ophthalmic diseases, such as glaucoma, retinitis, retinopathies, uveitis, ocular photophobia, and of inflammation and pain associated with acute injury to the eye tissue. Of particular interest among the uses of the present inventive S-[2-[(1-Iminoethyl)amino]ethyl]-2-methyl-L-cysteine maleate hydrochloride crystalline salt is the treatment of glaucoma, especially where symptoms of glaucoma are caused by the production of nitric oxide, such as in nitric oxide-mediated nerve damage.

S-[2-[(1-Iminoethyl)amino]ethyl]-2-methyl-L-cysteine maleate hydrochloride crystalline salt would also be useful in the treatment of pulmonary inflammation, such as that associated with viral infections and cystic fibrosis. The S-[2-[(1-Iminoethyl)amino]ethyl]-2-methyl-L-cysteine maleate hydrochloride crystalline salt would also be useful for the treatment of certain central nervous system disorders, such as cortical dementias including Alzheimer's disease, and central nervous system damage resulting from stroke, ischemia and trauma.

The S-[2-[(1-Iminoethyl)amino]ethyl]-2-methyl-L-cysteine maleate hydrochloride crystalline salt is useful as an anti-inflammatory agent, such as for the treatment of arthritis, with the additional benefit of having significantly less harmful side effects.

S-[2-[(1-Iminoethyl)amino]ethyl]-2-methyl-L-cysteine maleate hydrochloride crystalline salt would also be useful in the treatment of allergic rhinitis, respiratory distress syndrome, endotoxin shock syndrome, and atherosclerosis.

S-[2-[(1-Iminoethyl)amino]ethyl]-2-methyl-L-cysteine maleate hydrochloride crystalline salt would also be useful in the treatment of pain, including but not limited to postoperative pain, dental pain, muscular pain, and pain resulting from cancer. S-[2-[(1-Iminoethyl)amino]ethyl]-2-methyl-L-cysteine maleate hydrochloride crystalline salt would be useful for the prevention of dementias, such as Alzheimer's disease.

Besides being useful for human treatment, S-[2-[(1-Iminoethyl)amino]ethyl]-2-methyl-L-cysteine maleate hydrochloride crystalline salt is also useful for veterinary treatment of companion animals, exotic animals and farm animals, including mammals, rodents, and the like. More preferred animals include horses, dogs, and cats.

The present S-[2-[(1-Iminoethyl)amino]ethyl]-2-methyl-L-cysteine maleate hydrochloride crystalline salt may also be used in co-therapies, partially or completely, in place of other conventional antiinflammatory therapies, such as together with steroids, NSAIDs, COX-2 selective inhibitors, 5-lipoxygenase inhibitors, $LTB_4$ antagonists and $LTA_4$ hydrolase inhibitors.

Other conditions in which the S-[2-[(1-Iminoethyl)amino]ethyl]-2-methyl-L-cysteine maleate hydrochloride crystalline salt of the present invention will provide an advantage in inhibiting NO inhibition include cardiovascular ischemia, diabetes (type I or type II), congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (for example, secondary to cardiac arrest), multiple sclerosis and other central nervous system disorders mediated by NO, for example Parkinson's disease. Further neurodegenerative disorders in which NO inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia e.g. pre-senile dementia, and AIDS-related dementia, cachexia, Sydenham's chorea, Huntington's disease, Amyotrophic Lateral Sclerosis, Korsakoff's disease, imbecility relating to a cerebral vessel disorder, sleeping disorders, schizophrenia, depression, depression or other symptoms associated with Premenstrual Syndrome (PMS), anxiety and septic shock.

The S-[2-[(1-Iminoethyl)amino]ethyl]-2-methyl-L-cysteine maleate hydrochloride crystalline salt of the present invention will also be useful in the treatment of pain including somatogenic (either nociceptive or neuropathic), both acute and chronic. S-[2-[(1-Iminoethyl)amino]ethyl]-2-methyl-L-cysteine maleate hydrochloride crystalline salt could be used in any situation including neuropathic pain that a common NSAID or opioid analgesic would traditionally be administered.

Still other disorders or conditions which will be advantageously treated by the S-[2-[(1-Iminoethyl)amino]ethyl]-2-methyl-L-cysteine maleate hydrochloride crystalline salt of the present invention include treatment or prevention of opiate tolerance in patients needing protracted opiate analgesics, and benzodiazepine tolerance in patients taking benzodiazepines, and other addictive behavior, for example, nicotine addiction, alcoholism, and eating disorders.

The S-[2-[(1-Iminoethyl)amino]ethyl]-2-methyl-L-cysteine maleate hydrochloride crystalline salt of the present invention will also be useful in the treatment or prevention of drug withdrawal symptoms, for example treatment or prevention of symptoms of withdrawal from opiate, alcohol, or tobacco addiction.

The S-[2-[(1-Iminoethyl)amino]ethyl]-2-methyl-L-cysteine maleate hydrochloride crystalline salt may also be useful to prevent tissue damage when therapeutically combined with antibacterial or antiviral agents.

The S-[2-[(1-Iminoethyl)amino]ethyl]-2-methyl-L-cysteine maleate hydrochloride crystalline salt of the present invention will also be useful in inhibiting NO production from L-arginine including systemic hypotension associated with septic and/or toxic hemorrhagic shock induced by a wide variety of agents; therapy with cytokines such as TNF, IL-1 and IL-2; and as an adjuvant to short term immunosuppression in transplant therapy.

The present invention is further directed to the use of the S-[2-[(1-Iminoethyl)amino]ethyl]-2-methyl-L-cysteine maleate hydrochloride crystalline salt of the present invention for the treatment and prevention of neoplasias. The neoplasias that will be treatable or preventable by the S-[2-[(1-Iminoethyl)amino]ethyl]-2-methyl-L-cysteine maleate hydrochloride crystalline salt and methods of the present invention include brain cancer, bone cancer, a leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. Preferably, the neoplasia to be treated is selected from gastrointestinal cancer, liver cancer, bladder cancer, pancreas cancer, ovary cancer, prostate cancer, cervical cancer, lung cancer, breast cancer and skin cancer, such as squamous cell and basal cell cancers. The present S-[2-[(1-Iminoethyl)amino]ethyl]-2-methyl-L-cysteine maleate hydrochloride crystalline salt Form II and methods can also be used to treat the fibrosis which occurs with radiation therapy. The present S-[2-[(1-Iminoethyl)amino]ethyl]-2-methyl-L-cysteine maleate hydrochloride crystalline salt and methods can be used to treat subjects having adenomatous polyps, including those with familial adenomatous polyposis (FAP). Additionally, the present S-[2-[(1-Iminoethyl)amino]ethyl]-2-methyl-L-cysteine maleate hydrochloride crystalline salt and methods can be used to prevent polyps from forming in patients at risk of FAP.

Conjunctive treatment of a S-[2-[(1-Iminoethyl)amino]ethyl]-2-methyl-L-cysteine maleate hydrochloride crystalline salt of the present invention with another antineoplastic agent will produce a synergistic effect or alternatively reduce the toxic side effects associated with chemotherapy by reducing the therapeutic dose of the side effect-causing agent needed for therapeutic efficacy or by directly reducing symptoms of toxic side effects caused by the side effect-causing agent. S-[2-[(1-Iminoethyl)amino]ethyl]-2-methyl-L-cysteine maleate hydrochloride crystalline salt of the present invention will further be useful as an adjunct to radiation therapy to reduce side effects or enhance efficacy.

In the present invention, another agent which can be combined therapeutically with the S-[2-[(1-Iminoethyl)amino]ethyl]-2-methyl-L-cysteine maleate hydrochloride crystalline salt of the present invention includes any therapeutic agent which is capable of inhibiting the enzyme cyclooxygenase-2 ("COX-2"). Preferably such COX-2 inhibiting agents inhibit COX-2 selectively relative to the enzyme cyclooxygenase-1 ("COX-1"). Such a COX-2 inhibitor is known as a "COX-2 selective inhibitor". COX-2 selective inhibitors useful in therapeutic combination with the S-[2-[(1-Iminoethyl)amino]ethyl]-2-methyl-L-cysteine maleate hydrochloride crystalline salt of the present invention include celecoxib, valdecoxib, deracoxib, etoricoxib, rofecoxib, ABT-963 (2-(3, 4-difluorophenyl)-4-(3-hydroxy-3-methyl-1-butoxy)-5-[4-(methylsulfonyl)phenyl-3(2H)-pyridazinone; described in PCT Patent Application No. WO 00/24719), or meloxicam. S-[2-[(1-Iminoethyl)amino]ethyl]-2-methyl-L-cysteine maleate hydrochloride crystalline salt of the present invention can also be advantageously used in therapeutic combination with a prodrug of a COX-2 selective inhibitor, for example parecoxib.

Another chemotherapeutic agent which will be useful in combination with the S-[2-[(1-Iminoethyl)amino]ethyl]-2-methyl-L-cysteine maleate hydrochloride crystalline salt of the present invention can be selected, for example, from the following non-comprehensive and non-limiting list:

Alpha-difluoromethylornithine (DFMO), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa. Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, anti-neoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamiine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, uroguanylin, combretastatin, dolastatin, idarubicin, epirubicin, estramustine, cyclophosphamide, 9-amino-2-(S)-camptothecin, topotecan, irinotecan (Camptosar), exemestane, decapeptyl (tryptorelin), or an omega-3 fatty acid.

Examples of radioprotective agents which may be used in a combination therapy with the S-[2-[(1-Iminoethyl)amino]ethyl]-2-methyl-L-cysteine maleate crystalline salt Form II of this invention include AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

The S-[2-[(1'-Iminoethyl)amino]ethyl]-2-methyl-L-cysteine maleate hydrochloride crystalline salt of the present invention will also be useful in treatment or prevention of angiogenesis-related disorders or conditions, for example, tumor growth, metastasis, macular degeneration, and atherosclerosis.

In a further embodiment, the present invention also provides therapeutic combinations for the treatment or prevention of ophthalmic disorders or conditions such as glaucoma. For example the present inventive S-[2-[(1-Iminoethyl)amino]ethyl]-2-methyl-L-cysteine maleate hydrochloride crystalline salt advantageously will be used in therapeutic combination with a drug which reduces the intraocular pressure of patients afflicted with glaucoma. Such intraocular pressure-reducing drugs include without limitation latanoprost, travoprost, bimatoprost, or unoprostol. The therapeutic combination of the S-[2-[(1-Iminoethyl)amino]ethyl]-2-methyl-L-cysteine maleate hydrochloride crystalline salt of the present invention plus an intraocular pressure-reducing drug will be useful because each is believed to achieve its effects by affecting a different mechanism.

In another combination of the present invention, the present inventive S-[2-[(1-Iminoethyl)amino]ethyl]-2-methyl-L-cysteine maleate hydrochloride crystalline salt can be used in therapeutic combination with an antihyperlipidemic or cholesterol-lowering drug such as a benzothiepine or a benzothiazepine antihyperlipidemic drug. Examples of benzothiepine antihyperlipidemic drugs useful in the present inventive therapeutic combination can be found in U.S. Pat. No. 5,994,391, herein incorporated by reference. Some benzothiazepine antihyperlipidemic drugs are described in WO 93/16055. Alternatively, the antihyperlipidemic or cholesterol-lowering drug useful in combination with a compound of the present invention can be an HMG Co-A reductase inhibitor. Examples of HMG Co-A reductase inhibitors useful in the present therapeutic combination include, individually, benfluorex, fluvastatin, lovastatin, provastatin, simvastatin, atorvastatin, cerivastatin, bervastatin, ZD-9720 (described in PCT Patent Application No. WO 97/06802), ZD-4522 (CAS No. 147098-20-2 for the calcium salt; CAS No. 147098-18-8 for the sodium salt; described in European Patent No. EP 521471), BMS 180431 (CAS No. 129829-03-4), or NK-104 (CAS No. 141750-63-2). The therapeutic combination of the S-[2-[(1-Iminoethyl)amino]ethyl]-2-methyl-L-cysteine maleate hydrochloride crystalline salt of the present invention plus an antihyperlipidemic or cholesterol-lowering drug will be useful, for example, in reducing the risk of formation of atherosclerotic lesions in blood vessels. For example, atherosclerotic lesions often initiate at inflamed sites in blood vessels. It is established that antihyperlipidemic or cholesterol-lowering drug reduce risk of formation of atherosclerotic lesions by lowering lipid levels in blood. Without limiting the invention to a single mechanism of action, it is believed that one way the S-[2-[(1-Iminoethyl)amino]ethyl]-2-methyl-L-cysteine maleate hydrochloride crystalline salt of the present combination will work in concert to provide improved control of atherosclerotic lesions by, for example, reducing inflammation of the blood vessels in concert with lowering blood lipid levels.

In another embodiment of the invention, the present S-[2-[(1-Iminoethyl)amino]ethyl]-2-methyl-L-cysteine maleate hydrochloride crystalline salt can be used in combination with other compounds or therapies for the treatment of central nervous conditions or disorders such as migraine. For example, the present S-[2-[(1-Iminoethyl)amino]ethyl]-2-methyl-L-cysteine maleate hydrochloride crystalline salt can be used in therapeutic combination with caffeine, a 5-HT-1B/1D agonist (for example, a triptan such as sumatriptan, naratriptan, zolmitriptan, rizatriptan, almotriptan, or frovatriptan), a dopamine D4 antagonist (e.g., sonepiprazole), aspirin, acetaminophen, ibuprofen, indomethacin, naproxen sodium, isometheptene, dichloralphenazone, butalbital, an ergot alkaloid (e.g., ergotamine, dihydroergotamine, bromocriptine, ergonovine, or methyl ergonovine), a tricyclic antidepressant (e.g., amitriptyline or nortriptyline), a serotonergic antagonist (e.g., methysergide or cyproheptadine), a beta-andrenergic antagonist (e.g., propranolol, timolol, atenolol, nadolol, or metprolol), or a monoamine oxidase inhibitor (e.g., phenelzine or isocarboxazid).

A further embodiment provides a therapeutic combination of the S-[2-[(1-Iminoethyl)amino]ethyl]-2-methyl-L-cysteine maleate hydrochloride crystalline salt of the present invention with an opioid compound. Opioid compounds useful in this combination include without limitation morphine, methadone, hydromorphone, oxymorphone, levorphanol, levallorphan, codeine, dihydrocodeine, dihydrohydroxycodeinone, pentazocine, hydrocodone, oxycodone, nalmefene, etorphine, levorphanol, fentanyl, sufentanil, DAMGO, butorphanol, buprenorphine, naloxone, naltrexone, CTOP, diprenorphine, beta-funaltrexamine, naloxonazine, nalorphine, pentazocine, nalbuphine, naloxone benzoylhydrazone, bremazocine, ethylketocyclazocine, U50,488, U69,593, spiradoline, nor-binaltorphimine, naltrindole, DPDPE, [D-la$^2$, glu$^4$]deltorphin, DSLET, met-enkephalin, leu-enkaphalin, beta-endorphin, dynorphin A, dynorphin B, and alpha-neoendorphin. An advantage to the combination of the S-[2-[(1-Iminoethyl)amino]ethyl]-2-methyl-L-cysteine maleate hydrochloride crystalline salt of the present invention with an opioid compound is that the present inventive S-[2-[(1-Iminoethyl)amino]ethyl]-2-methyl-L-cysteine maleate hydrochloride crystalline salt will allow a reduction in the dose of the opioid compound, thereby reducing the risk or severity of opioid side effects, such as opioid addiction.

A further embodiment provides four mechanistically distinct novel crystallization process designs for the preparation of the S-[2-[(1-Iminoethyl)amino]ethyl]-2-methyl-L-cysteine maleate hydrochloride crystalline salt of the present invention with tailored bulk powder characteristics for easy to prepare pharmaceutical compositions comprising S-[2-[(1-Iminoethyl)amino]ethyl]-2-methyl-L-cysteine maleate hydrochloride crystalline salt together with a pharmaceutically acceptable carrier.

ILLUSTRATIVE EXAMPLES

Methods to make S-[2-[(1-iminoethyl)amino]ethyl]-2-methyl-L-cysteine dihydrochloride are known and described in commonly assigned U.S. Pat. No. 6,403,830, incorporated herein by reference. S-[2-[(1-Iminoethyl)amino]ethyl]-2-methyl-L-cysteine free zwitterion is described in co-pending U.S. Application Ser. No. 60/453,798, incorporated herein by reference. Crystalline S-[2-[(1-Iminoethyl)amino]ethyl]-2-methyl-L-cysteine maleate Form I is described in co-pending U.S. Application Ser. No. 60/453,796, incorporated herein by reference. Crystalline S-[2-[(1-Iminoethyl)amino]ethyl]-2-methyl-L-cysteine maleate Form II is described in co-pending U.S. Application Ser. No. 60/453,782, incorporated herein by reference.

Characterization of S-[2-[(1-Iminoethyl)amino] ethyl]-2-methyl-L-cysteine maleate hydrochloride S-[2-[(1-Iminoethyl)amino]ethyl]-2-methyl-L-cysteine maleate hydrochloride crystals are birefringent with positive elongation when analyzed by polarized light microscopy. S-[2-[(1-Iminoethyl)amino]ethyl]-2-methyl-L-cysteine maleate hydrochloride crystalline salt has an aqueous solubility in excess of 150 mg ml$^{-1}$.

FIG. 1 is powder x-ray pattern of two samples (Examples 9 and 20) of S-[2-[(1-Iminoethyl)amino]ethyl]-2-methyl-L-cysteine maleate hydrochloride. Both diffraction patterns help establish characteristic peaks useful in characterizing crystalline S-[2-[(1-Iminoethyl)amino]ethyl]-2-methyl-L-cysteine maleate hydrochloride.

Figure 2:
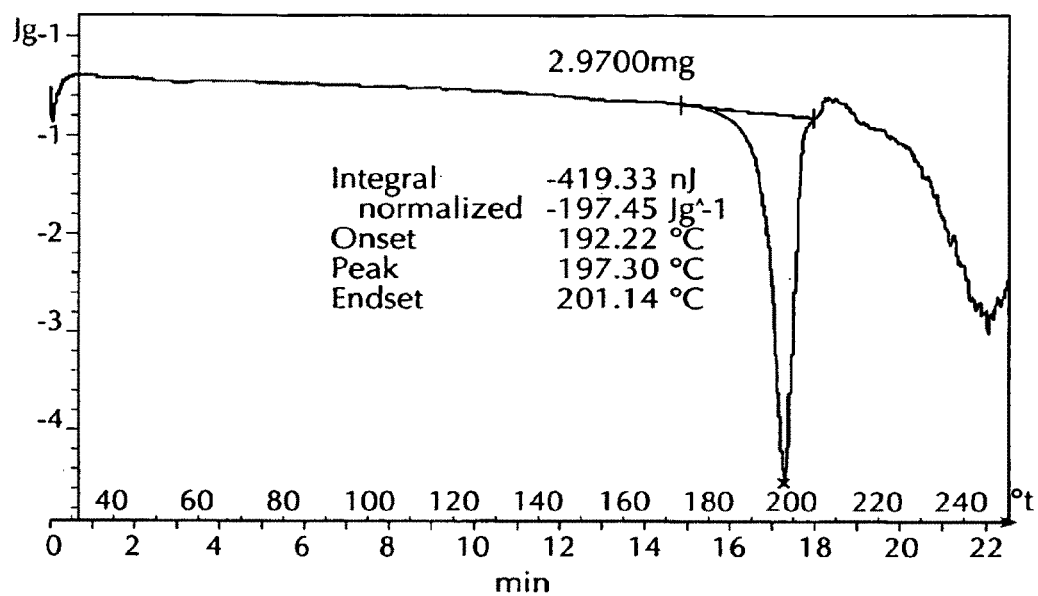
FIG. 2 is a graph of a differential scanning calorimetry study of a sample (Example 11) of crystalline S-[2-[(1-Iminoethyl)amino]ethyl]-2-methyl-L-cysteine maleate hydrochloride.
Figure 3:
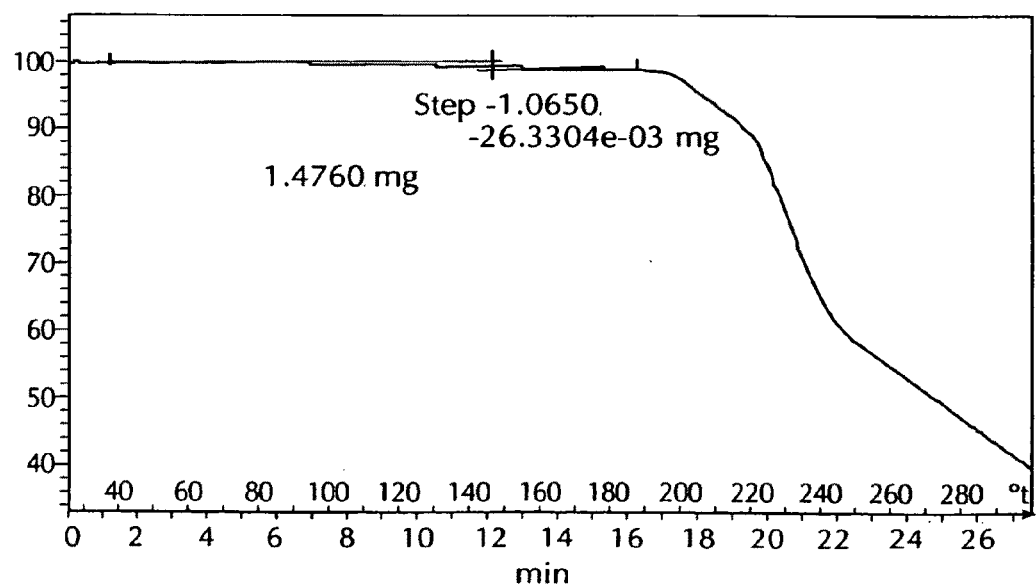
FIG. 3 is a thermogravimetric plot of a sample (Example 11) of crystalline S-[2-[(1-Iminoethyl)amino]ethyl]-2-methyl-L-cysteine maleate hydrochloride.

FIG. 2 is a graph of a differential scanning calorimetry study of a sample of the crystalline S-[2-[(1-Iminoethyl) amino]ethyl]-2-methyl-L-cysteine maleate hydrochloride. It shows a single melt/decomposition thermal event at 197.30° C. with an associated enthalpy of 134.92 J gram$^{-1}$. Since the single thermal event is a composite of thermal degradation of maleic acid in crystalline S-[2-[(1-Iminoethyl)amino]ethyl]-2-methyl-L-cysteine maleate hydrochloride and the melting of the residual crystalline solids, both the peak temperature and enthalpy can vary depending on the analysis conditions such as the sample size, heating rate and the method for sample preparation. FIG. 3 is a thermogravimetric (TGA) plot of a sample of the crystalline S-[2-[(1-Iminoethyl) amino]ethyl]-2-methyl-L-cysteine maleate hydrochloride. TGA shows a weight loss of approximately 1% over the 40-180° C. temperature range.

Figure 4:
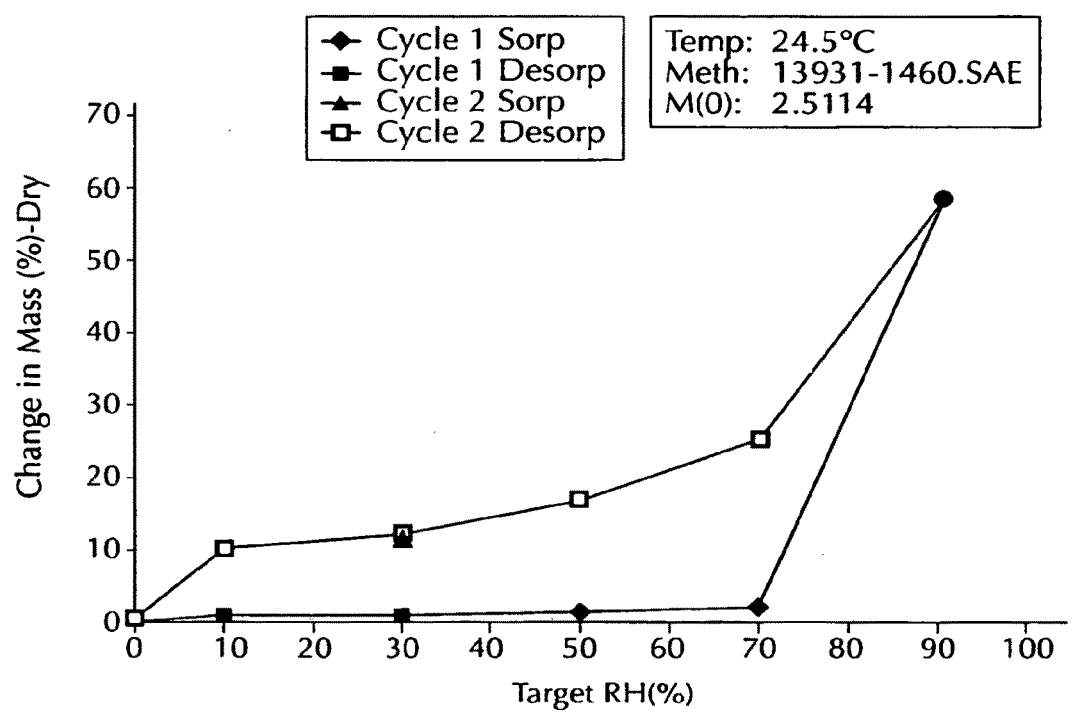
FIG. 4 is a plot of a moisture sorption study of a sample (Example 10) of crystalline S-[2-[(1-Iminoethyl)amino]ethyl]-2-methyl-L-cysteine maleate hydrochloride.

FIG. 4 is a plot of a moisture sorption study of the crystalline S-[2-[(1-Iminoethyl)amino]ethyl]-2-methyl-L-cysteine maleate hydrochloride. Moisture sorption of the crystalline S-[2-[(1-Iminoethyl)amino]ethyl]-2-methyl-L-cysteine maleate hydrochloride 25° C., by DVS moisture balance, showed a moisture update of approximately 1.5% between 0 and 70% relative humidity (R.H.). Between 70 and 9% R.H., another 58% moisture was taken up by the solids. It is presumed that at 90% R.H. the crystal structure was destroyed to produce highly hygroscopic amorphous solids. During the de-sorption cycle (from 90 to 30% R.H.), these solids transformed into a mixture of form II of the crystalline S-[2-[(1-Iminoethyl)amino]ethyl]-2-methyl-L-cysteine maleate and amorphous zwitterion with excess hydrogen chloride. Subsequent de-sorption and re-sorption behavior was very similar to form II of the crystalline S-[2-[(1-Iminoethyl)amino]

ethyl]-2-methyl-L-cysteine maleate. Powder x-ray analysis on the solids at the end of the experiment confirmed the presence of both form II the crystalline S-[2-[(1-Iminoethyl)amino]ethyl]-2-methyl-L-cysteine maleate and amorphous solids.

Figure 5:
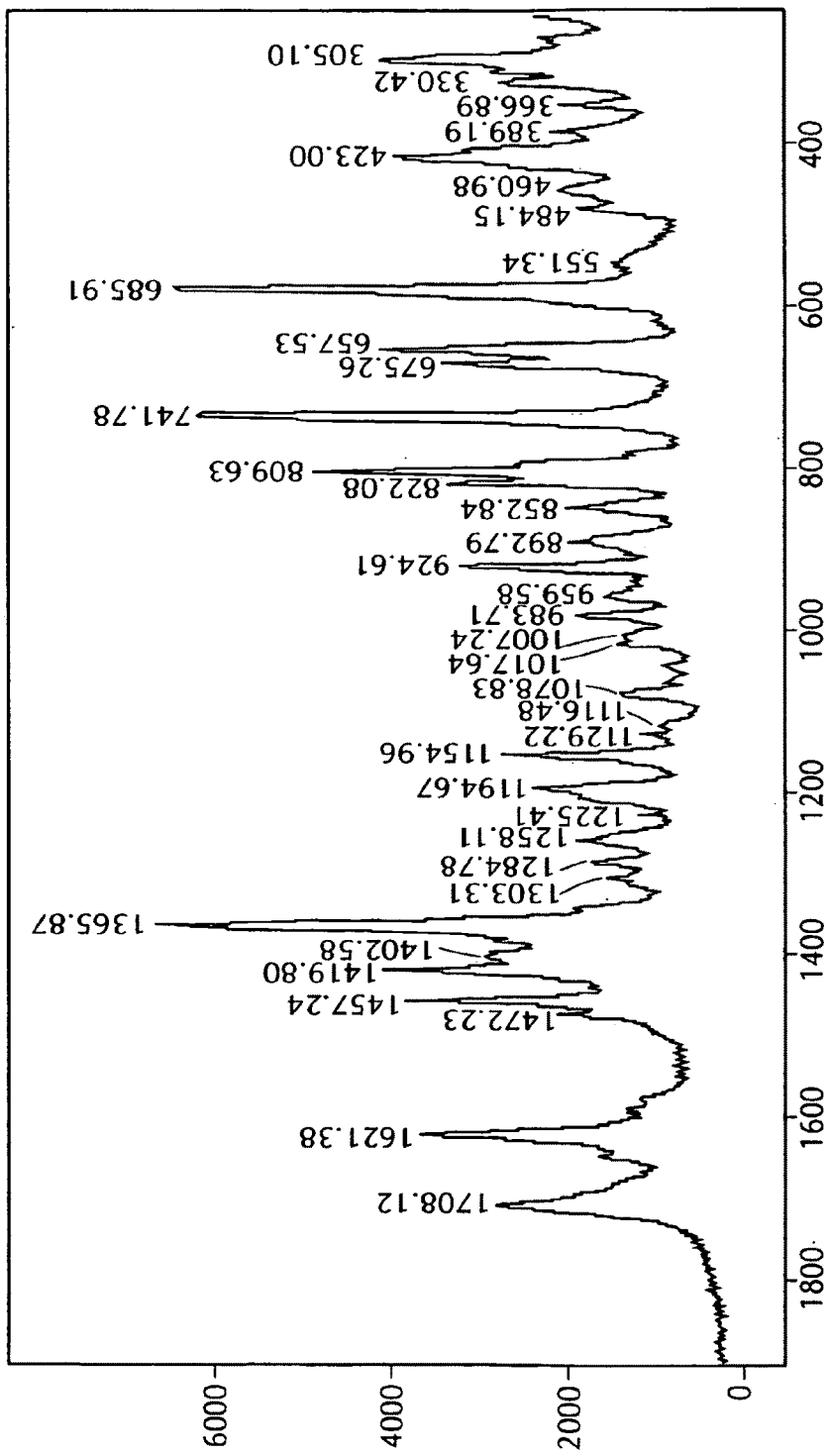
FIG. 5 shows a Raman spectrum of the crystalline S-[2-[(1-Iminoethyl)amino]ethyl]-2-methyl-L-cysteine maleate hydrochloride obtained from a sample from Example 20.

FIG. 5 shows the Raman spectrum of the crystalline S-[2-[(1-Iminoethyl)amino]ethyl]-2-methyl-L-cysteine maleate hydrochloride made in Example 20. Briefly, the Raman spectrum is a vibrational signature of a molecule or complex system. Its origin lies in the inelastic collisions between the molecules and photons, which are the particles of light composing a light beam. The collision between the molecules and the photons leads to an exchange of energy with consequent change in energy and hence wavelength of the photon. Thus, a Raman spectrum is a set of very narrow spectral lines emitted from object molecules when illuminated by an incident light. The width of each spectral line is strongly affected by the spectral width of the incident light and hence tightly monochromatic light sources, such as lasers, are used. The wavelength of each Raman line is expressed as a wave number-shift from the incident light, which is the difference between the inverse wavelength of the Raman line and the incident light. The wave number-shift, not the absolute wavelength, of the Raman lines is specific to particular atomic groups in molecules. Raman spectra measure the vibration states of molecules, which are determined by their molecular structure.

Crystallization of S-[2-[(1-Iminoethyl)amino]ethyl]-2-methyl-L-cysteine maleate hydrochloride The diverse selection of examples reported here for the crystallization of mixed salt is organized in three main sub-sections. The first sub-section, Examples 1-6, presents the account of experiments that failed to produce polymorphically pure crystalline S-[2-[(1-Iminoethyl)amino]ethyl]-2-methyl-L-cysteine maleate hydrochloride. In most of these experiments mixtures with Form I of S-[2-[(1-Iminoethyl)amino]ethyl]-2-methyl-L-cysteine maleate were obtained. A brief discussion on the reasons for the failure to obtain polymorphically pure crystalline S-[2-[(1-Iminoethyl)amino]ethyl]-2-methyl-L-cysteine maleate hydrochloride is also included at the end of the sub-section.

External crystal shape of the mixed salt defines the next two main sub-sections. This particular product attribute is driven by distinct underlying crystallization mechanisms and has major implications for the subsequent development of a pharmaceutical composition comprising S-[2-[(1-Iminoethyl)amino]ethyl]-2-methyl-L-cysteine maleate hydrochloride together with a pharmaceutically acceptable carrier. The two distinct shapes, for the purposes of this invention from here on are referred to as "randomly packed agglomerates" usually but not necessarily non-spherical in overall appearance and "orderly packed agglomerates" usually but not necessarily spherical in overall appearance. In general, primary crystals making up the agglomerate have smaller aspect ratios for the orderly packed agglomerates when compared to the primary crystals making up randomly packed agglomerates. For the purposes of this invention, aspect ratio is defined as the ratio of the long ferret to the short ferret.

First, the examples pertinent to the crystallization of "randomly packed agglomerates," Examples 7-19 are discussed. This is followed by a discussion on the underlying crystallization mechanism directing the formation of this particular crystal shape. Also included is a detailed definition of "phase separation" for the purpose of this invention.

Finally, Examples 20-30, the account of various experiments that followed the diverse variants of processes for the "orderly packed agglomerates" is summarized.

FEEDSTOCK DEFINITIONS

The zwitterion; S-[2-[(1-Iminoethyl)amino]ethyl]-2-methyl-L-cysteine used in all the examples reported here was either obtained as amorphous freeze dried solids or solutions in DMF.

Solid S-[2-[(1-Iminoethyl)amino]ethyl]-2-methyl-L-cysteine would be referred to as amorphous freeze dried S-[2-[(1-Iminoethyl)amino]ethyl]-2-methyl-L-cysteine from here on. In most cases, amorphous freeze dried S-[2-[(1-Iminoethyl)amino]ethyl]-2-methyl-L-cysteine contained some hydrogen-chloride (HCl). Molar equivalents of HCl to S-[2-[(1-Iminoethyl)amino]ethyl]-2-methyl-L-cysteine would be specified in each example for the specific lot of the amorphous freeze dried S-[2-[(1-Iminoethyl)amino]ethyl]-2-methyl-L-cysteine used for the crystallization of S-[2-[(1-Iminoethyl)amino]ethyl]-2-methyl-L-cysteine maleate hydrochloride.

The first DMF/S-[2-[(1-Iminoethyl)amino]ethyl]-2-methyl-L-cysteine stock solution had an approximate composition of: S-[2-[(1-Iminoethyl)amino]ethyl]-2-methyl-L-cysteine 11.7% w/w; water 0.2% w/w; maleic acid 12.4% w/w; and chloride 1.0%. Variability of 10% could be expected for each component of this solution. The aforementioned concentration of maleic acid and chloride in the solution represents approximately 2.0 and 0.5 molar equivalents respectively for each equivalent of S-[2-[(1-Iminoethyl)amino]ethyl]-2-methyl-L-cysteine. This solution would be referred to as the primary DMF solution of S-[2-[(1-Iminoethyl)amino]ethyl]-2-methyl-L-cysteine from here on.

The other stock solution of S-[2-[(1-Iminoethyl)amino]ethyl]-2-methyl-L-cysteine in DMF had an approximate composition of: S-[2-[(1-Iminoethyl)amino]ethyl]-2-methyl-L-cysteine 11.7% w/w; water 2.83% w/w; maleic acid 14.88% w/w; and chloride 1.0%. The aforementioned concentration of maleic acid and chloride in the solution represents approximately 2.2 and 0.5 molar equivalents respectively for each equivalent of S-[2-[(1-Iminoethyl)amino]ethyl]-2-methyl-L-cysteine. This solution is referred to as the secondary DMF solution of S-[2-[(1-Iminoethyl)amino]ethyl]-2-methyl-L-cysteine from here on.

Examples of Failed Experiments with Respect to Polymorphic Purity

Six distinct experiments produced mixtures of crystalline S-[2-[(1-Iminoethyl)amino]ethyl]-2-methyl-L-cysteine maleate hydrochloride with crystalline Form I of S-[2-[(1-Iminoethyl)amino]ethyl]-2-methyl-L-cysteine maleate. The small quantities of the latter were readily detected by the DSC analysis.

Example 1

In Example 1, 614 mg of 0.25 eq. HCl containing amorphous freeze dried S-[2-[(1-Iminoethyl)amino]ethyl]-2-methyl-L-cysteine (containing approximately 10% water), 648 mg of maleic acid, 988 mg of DI water and 2460.7 mg of DMF were added to a 25 ml scintillation vial equipped with a magnetic stirrer. The suspension was stirred to affect a clear solution. 16 ml of acetonitrile were slowly added to the solution in 1.0 ml aliquots over 50 minutes. Turbidity subsided completely upon the completion of the charge. The vial was stirred at room temperature for seventeen hours and then heated to 60° C. in forty minutes. It was stirred at this temperature for forty hours and then two ml of acetonitrile were added. The slurry was stirred for another hour at 60° C. and then cooled to 25° C. in one hour and stirred for four hours. The slurry was discharged on a fine frit sintered glass funnel. The cake was washed with 2 ml of acetonitrile and air dried for half an hour. Solids were placed in a vacuum oven at 55° C. and 28 inches Hg for 24 hours. PXRD analysis on the product did not show any appreciable amount of Form I of S-[2-[(1-Iminoethyl)amino]ethyl]-2-methyl-L-cysteine maleate mixed in with the S-[2-[(1-Iminoethyl)amino]ethyl]-2-methyl-L-cysteine maleate hydrochloride, however DSC analysis indicated that some Form I of S-[2-[(1-Iminoethyl)amino]ethyl]-2-methyl-L-cysteine maleate was present in the product.

Example 2

Example 2 involved adding 201 mg of 0.25 eq. HCl containing amorphous freeze dried S-[2-[(1-Iminoethyl)amino]ethyl]-2-methyl-L-cysteine (containing approximately 10% water), 209 mg of maleic acid and 1120 mg of DMF to a 12 ml vial equipped with a magnetic stirrer. The suspension was stirred to affect a clear solution. 5 ml of acetonitrile were slowly added to the solution in 1.0 ml aliquots over 50 minutes. Turbidity did not completely subside, nevertheless 7 mg of Form I of S-[2-[(1-Iminoethyl)amino]ethyl]-2-methyl-L-cysteine maleate were added as seed crystals. The vial was stirred at room temperature for six hours and then heated to 60° C. in forty minutes. It was stirred at this temperature for forty hours. The slurry was discharged on a fine frit sintered glass funnel. The cake was washed with 2 ml of acetonitrile and air dried for half an hour. Solids were placed in a vacuum oven at 55° C. and 28 inches Hg for 24 hours. PXRD analysis on the product did not show any appreciable amount of Form I of S-[2-[(1-Iminoethyl)amino]ethyl]-2-methyl-L-cysteine maleate mixed in with S-[2-[(1-Iminoethyl)amino]ethyl]-2-methyl-L-cysteine maleate hydrochloride, however DSC analysis indicated that Form I of S-[2-[(1-Iminoethyl)amino]ethyl]-2-methyl-L-cysteine maleate was present in the product.

Example 3

The objective of Example 3 was to determine if seeding with Form I of S-[2-[(1-Iminoethyl)amino]ethyl]-2-methyl-L-cysteine maleate had contributed to polymorphically impure product in Example 2. 203 mg of 0.25 eq. HCl containing amorphous freeze dried S-[2-[(1-Iminoethyl)amino]ethyl]-2-methyl-L-cysteine (containing approximately 10% water), 208 mg of maleic acid and 1137 mg of DMF were added to a 12 ml vial equipped with a magnetic stirrer. The suspension was stirred to affect a clear solution. 4 ml of acetonitrile were slowly added to the solution in 1.0 ml aliquots over 50 minutes. Turbidity completely subsided upon the completion of reduced acetonitrile charge. The vial was stirred at room temperature for six hours and then heated to 60° C. in forty minutes. It was stirred at this temperature for forty hours and then cooled to room temperature. The slurry was discharged on a fine frit sintered glass funnel. The cake was washed with 2 ml of acetonitrile and air dried for half an hour. Solids were placed in a vacuum oven at 55° C. and 28 inches Hg for 24 hours. PXRD analysis on the product did not show any appreciable amount of Form I of S-[2-[(1-Iminoethyl)amino]ethyl]-2-methyl-L-cysteine maleate mixed in with S-[2-[(1-Iminoethyl)amino]ethyl]-2-methyl-L-cysteine maleate hydrochloride, however DSC analysis indicated that Form I of S-[2-[(1-Iminoethyl)amino]ethyl]-2-methyl-L-cysteine maleate was present in the product.

Example 4

The objective of Example 4 was to study the crystallization behavior at sub-ambient temperatures. 201 mg of 0.25 eq. HCl containing amorphous freeze dried S-[2-[(1-Iminoethyl)amino]ethyl]-2-methyl-L-cysteine (containing approximately 10% water), 209 mg of maleic acid and 1141 mg of DMF were added to a 12 ml vial equipped with a magnetic stirrer. The suspension was stirred to affect a clear solution. 4 ml of acetonitrile were slowly added to the solution in 1.0 ml aliquots over 50 minutes. Turbidity subsided completely upon the completion of the charge. The vial was cooled to −5° C. and stirred for twenty-four hours. The solution had turned into very thick "gel-like" slurry of crystalline solids. 4 ml of acetonitrile were added to the slurry to dilute it. It was then heated back to 25° C. and stirred for four hours. The slurry was discharged on a fine frit sintered glass funnel. The cake was washed with 2 ml of acetonitrile and air dried for half an hour. Solids were placed in a vacuum oven at 40° C. and 28 inches Hg for 24 hours. PXRD analysis on the product did not show any appreciable amount of Form I of S-[2-[(1-Iminoethyl)amino]ethyl]-2-methyl-L-cysteine maleate mixed in with S-[2-[(1-Iminoethyl)amino]ethyl]-2-methyl-L-cysteine maleate hydrochloride, however DSC analysis indicated that Form I of S-[2-[(1-Iminoethyl)amino]ethyl]-2-methyl-L-cysteine maleate was present in the product.

Example 5

In Example 5, maleic acid content of the system was reduced by 25%. It involved adding 304 mg of 0.25 eq. HCl containing amorphous freeze dried S-[2-[(1-Iminoethyl)amino]ethyl]-2-methyl-L-cysteine (containing approximately 10% water), 241 mg of maleic acid and 1659 mg of DMF to a 12 ml vial equipped with a magnetic stirrer. The suspension was stirred to affect a clear solution. 4 ml of acetonitrile were slowly added to the solution in 1.0 ml aliquots over 50 minutes. The turbidity of the system converted into a solid viscous mass at the bottom of the vial after the completion of acetonitrile charge. The vial was heated to 60° C. in forty minutes. Within two and a half hours at 60° C., solids were observed in the vial. However, they seemed stuck to the walls of the vial and were therefore scrapped with a spatula and suspended back in the solution. The slurry was stirred at this temperature for nineteen hours and then discharged on a fine frit sintered glass funnel. The cake was very wet. It was re-suspended in 2 ml of acetonitrile and then washed. The cake was air dried for half an hour. Solids were then air dried in an open crystallization dish for 2 hours. PXRD analysis on the product showed appreciable amount of Form I of S-[2-[(1-Iminoethyl)amino]ethyl]-2-methyl-L-cysteine maleate mixed in with S-[2-[(1-Iminoethyl)amino]ethyl]-2-methyl-L-cysteine maleate hydrochloride. DSC analysis confirmed PXRD results.

Example 6

The objective of Example 6 was to increase yield by using a modified addition regime for acetonitrile at levels similar to those in Example 5. It involved adding 301 mg of 0.25 eq. HCl containing amorphous freeze dried S-[2-[(1-Iminoethyl)amino]ethyl]-2-methyl-L-cysteine (containing approximately 10% water), 241 mg of maleic acid and 1660 mg of DMF to a 12 ml vial equipped with a magnetic stirrer. The suspension was stirred to affect a clear solution. 3 ml of acetonitrile were slowly added to the solution in 1.0 ml aliquots over 50 minutes. The turbidity of the system subsided on the completion of acetonitrile charge and crystals were observed within 30 minutes. The slurry was stirred at room temperature for three hours and then one ml of acetonitrile was added. Stirring continued at room temperature for another nineteen hours. The slurry was discharged on a fine frit sintered glass funnel. The cake was washed with 2 ml of acetonitrile and air dried for half an hour. Solids were then air dried in an open crystallization dish for 2 hours. PXRD analysis on the product did not show any appreciable amount of Form I of S-[2-[(1-Iminoethyl)amino]ethyl]-2-methyl-L-cysteine maleate mixed in with S-[2-[(1-Iminoethyl)amino]ethyl]-2-methyl-L-cysteine maleate hydrochloride, however DSC analysis indicated that Form I of S-[2-[(1-Iminoethyl)amino]ethyl]-2-methyl-L-cysteine maleate was present in the product.

Discussion of Examples 1-6

Thermal analysis on the intermediate solid samples withdrawn during various stages of the experiments reported above indicated that Form I of S-[2-[(1-iminoethyl)amino]ethyl]-2-methyl-L-cysteine maleate crystallized during the cool down or the extended hold periods at any of the hold temperatures reported above. This implies secondary nucleation of Form I of S-[2-[(1-Iminoethyl)amino]ethyl]-2-methyl-L-cysteine maleate during the latter stages of crystallization. Without wishing to be bound by any theory, it is believed that this is explained because during the hold periods, the system is completely depleted of HCl through the formation of crystalline S-[2-[(1-Iminoethyl)amino]ethyl]-2-methyl-L-cysteine maleate hydrochloride. However, there is still 0.5 equivalents of S-[2-[(1-Iminoethyl)amino]ethyl]-2-methyl-L-cysteine and 1.75 equivalents of maleic acid in the system at concentrations probably above the solubility of Form I of S-[2-[(1-Iminoethyl)amino]ethyl]-2-methyl-L-cysteine maleate. As the system attempts to de-saturate further through cooling, anti-solvent addition, hold periods or reduced maleic acid content, super-saturation with respect to Form I of S-[2-[(1-Iminoethyl)amino]ethyl]-2-methyl-L-cysteine maleate is depleted through its crystallization in the presence of all the heterogeneous surfaces offered by S-[2-[(1-Iminoethyl)amino]ethyl]-2-methyl-L-cysteine maleate hydrochloride crystals.

In summary, for experiments under HCl deficient conditions, any attempt to increase the super-saturation of the system at any stage through anti-solvent addition, cooling or reducing maleic acid content can lead to the loss of control with respect to the polymorphic purity of the product. In a DMF/acetonitrile system in such a hydrochloride deficient state, mixtures with Form I of S-[2-[(1-Iminoethyl)amino]ethyl]-2-methyl-L-cysteine maleate can be expected.

Examples of Randomly Packed Agglomerates

Examples 7, 8 and 9 had stoichiometric amounts of HCl in relation to S-[2-[(1-Iminoethyl)amino]ethyl]-2-methyl-L-cysteine to crystallize S-[2-[(1-Iminoethyl)amino]ethyl]-2-methyl-L-cysteine maleate hydrochloride. Example 7 and 8 represent experiments performed at low water and acetonitrile levels. Example 9 is an experiment conducted at the standard water content and acetonitrile levels.

Experiments captured in Examples 10 through 19 were conducted to demonstrate that S-[2-[(1-Iminoethyl)amino]ethyl]-2-methyl-L-cysteine maleate hydrochloride could be crystallized and isolated over a wide range of values for the molar equivalents of HCl in relation to S-[2-[(1-Iminoethyl)amino]ethyl]-2-methyl-L-cysteine.

Examples 10, 11, 12 and 13 were all performed at 26% of the required amount of HCl in relation to S-[2-[(1-Iminoethyl)amino]ethyl]-2-methyl-L-cysteine to crystallize S-[2-[(1-Iminoethyl)amino]ethyl]-2-methyl-L-cysteine maleate hydrochloride. Example 13 involved direct precipitation of S-[2-[(1-Iminoethyl)amino]ethyl]-2-methyl-L-cysteine maleate hydrochloride, while Examples 10 through 12 involved precipitation of either the Form I or II of S-[2-[(1-Iminoethyl)amino]ethyl]-2-methyl-L-cysteine maleate, followed by solution mediated phase conversion to crystalline S-[2-[(1-Iminoethyl)amino]ethyl]-2-methyl-L-cysteine maleate hydrochloride through heating and or extended hold periods at select temperatures.

Examples 14, 15 and 16 were all performed at 50% of the required amount of HCl in relation to S-[2-[(1-Iminoethyl)amino]ethyl]-2-methyl-L-cysteine to crystallize S-[2-[(1-Iminoethyl)amino]ethyl]-2-methyl-L-cysteine maleate hydrochloride. Examples 14 and 15 involved direct precipitation of S-[2-[(1-Iminoethyl)amino]ethyl]-2-methyl-L-cysteine maleate hydrochloride, while Example 14 involved precipitation of either the Form I or II of S-[2-[(1-Iminoethyl)amino]ethyl]-2-methyl-L-cysteine maleate, followed by solution mediated phase conversion to crystalline S-[2-[(1-Iminoethyl)amino]ethyl]-2-methyl-L-cysteine maleate hydrochloride through heating and/or extended hold periods at select temperatures.

Examples 17, 18 and 19 were performed at HCl levels higher than those required for stoichiometric considerations to convert S-[2-[(1-Iminoethyl)amino]ethyl]-2-methyl-L-cysteine into crystalline S-[2-[(1-Iminoethyl)amino]ethyl]-2-methyl-L-cysteine maleate hydrochloride.

Example 7

To 126.1 grams of the primary DMF solution of S-[2-[(1-Iminoethyl)amino]ethyl]-2-methyl-L-cysteine, 1.46 grams of de-ionized water were added in order to take the water content of the primary DMF solution of S-[2-[(1-Iminoethyl)amino]ethyl]-2-methyl-L-cysteine to 1.63%. 125.5 grams of this solution was charged to a 500 ml jacketed reactor with agitation set at 354 rpm. A total of 126.58 grams of acetonitrile were added to the reactor through a pump at a rate of 1.4 ml per minute over two hours. Crystals had formed during the addition period. The system was stirred for a total of 53 hours and then the slurry was discharged and filtered on a fine frit sintered glass funnel. Filtration was extremely fast. The cake was rinsed with 83 ml of acetonitrile and air dried for twenty-four hours. It weighed 13.48 grams.

Example 8

To 7.5 grams of the primary DMF solution of S-[2-[(1-Iminoethyl)amino]ethyl]-2-methyl-L-cysteine, 109 micro-liters of de-ionized water were added in order to take the water content of the primary DMF solution of S-[2-[(1-Iminoethyl)amino]ethyl]-2-methyl-L-cysteine to 1.63%. This solution was charged to a 25 ml round bottom flask stirred with a magnetic bead. A total of 7.85 grams of acetonitrile were added to the flask in 0.5 ml aliquots every three minutes over 54 minutes. The system was stirred for a total of 72 hours and then and then the slurry was discharged and filtered on a 15 ml fine frit sintered glass funnel.

Filtration was slow. The cake was rinsed with 4 ml of acetonitrile and air dried for twenty-four hours. Some solids had crystallized out on the walls of the round bottom flask. They were isolated separately. Mass balance on the all the isolated solids indicated that the solids on the wall represented 65% of the entire product. SEM photomicrographs of the solids from the slurry and the walls confirmed that this experiments produced a "randomly packed agglomerate" shape for the crystalline S-[2-[(1-Iminoethyl)amino]ethyl]-2-methyl-L-cysteine maleate hydrochloride.

Example 9

Example 9 was performed with amorphous freeze dried S-[2-[(1-Iminoethyl)amino]ethyl]-2-methyl-L-cysteine (containing approximately 10% water) that did not contain any HCl. The procedure involved adding 565 mg of amorphous freeze dried S-[2-[(1-Iminoethyl)amino]ethyl]-2-methyl-L-cysteine (containing approximately 10% water), 599 mg of maleic acid, 105 mg of 37% concentrated HCl (aqueous) and 2969 mg of DMF to a 12 ml vial equipped with a magnetic stirrer. The suspension was stirred to affect a clear solution. 7.5 ml of acetonitrile were slowly added to the solution in 0.5 ml aliquots over 25 minutes. Significant crystallization occurred during the addition of acetonitrile. The vial was stirred at room temperature for twenty-two hours and then filtered on a fine frit sintered glass funnel. The cake was washed with 4 ml of acetonitrile and air dried for half an hour. Solids were placed in a vacuum oven at 55° C. and 28 inches Hg for 24 hours.

Figure 6:
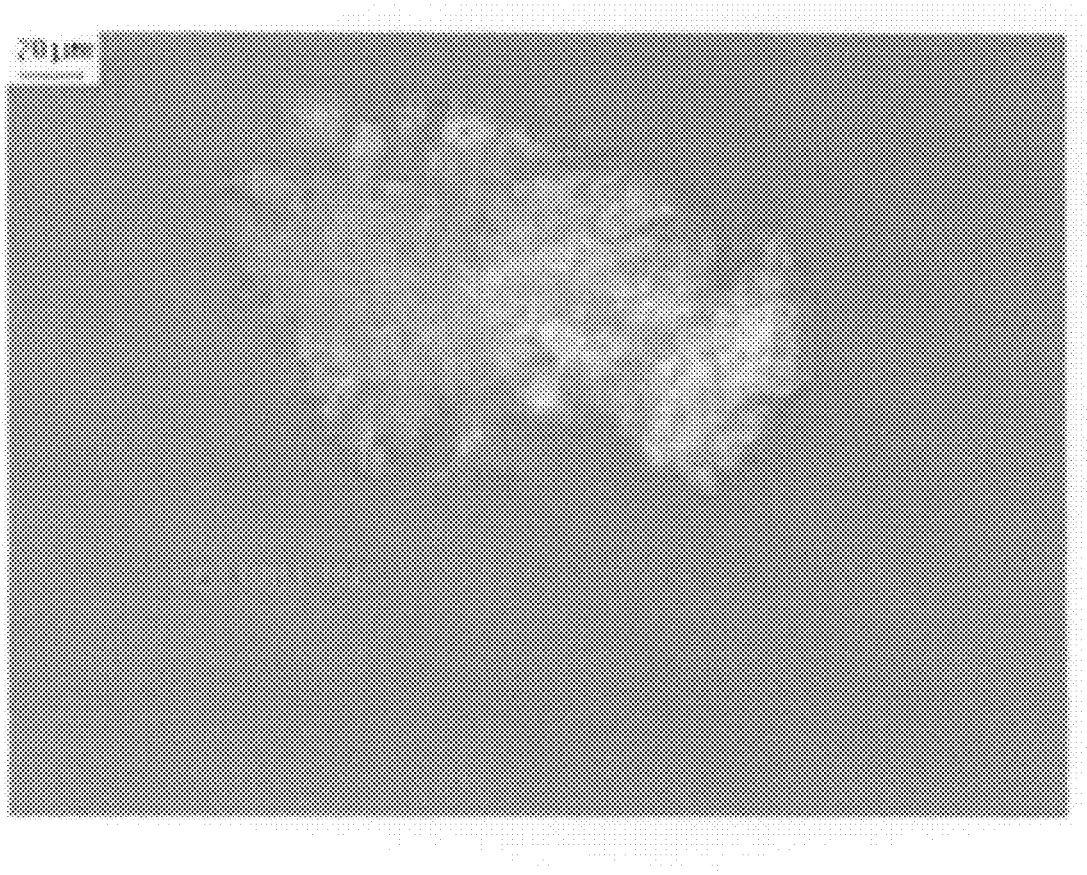
FIG. 6 is a photomicrograph of the crystalline S-[2-[(1-Iminoethyl)amino]ethyl]-2-methyl-L-cysteine maleate hydrochloride from Example 9.
Figure 7A:
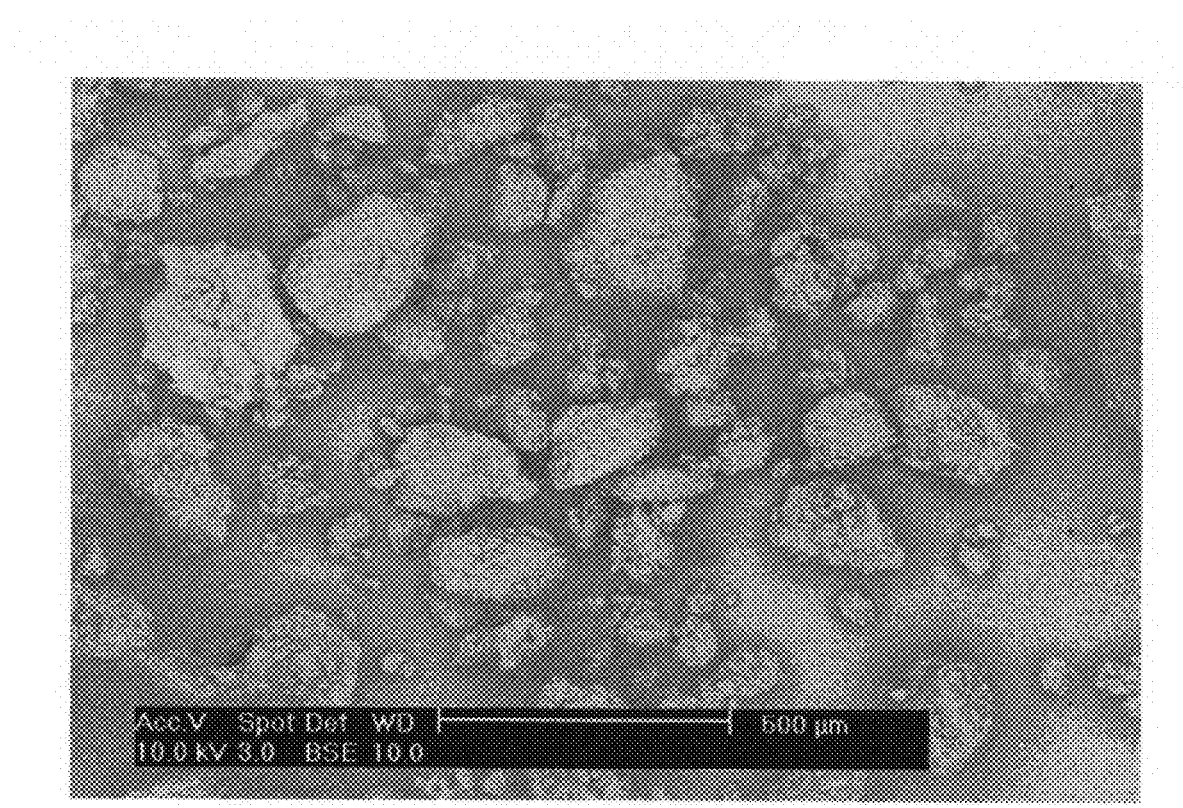
Figure 7B:
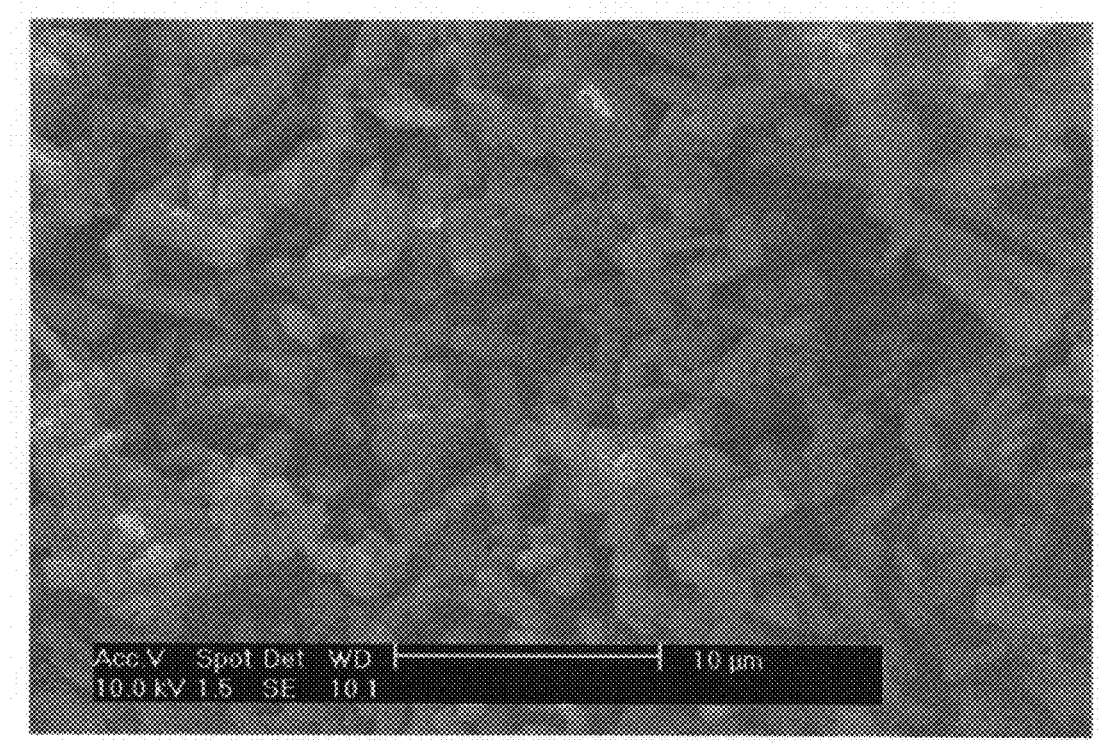
FIG. 7B shows the random packing of crystals within the agglomerates.

FIG. 6 shows a photomicrograph of the product. It seems that the solids are randomly packed agglomerates made of very small, perhaps sub-micron primary crystals. All the analytical data on oven-dried solids from this experiment confirmed its identity as crystalline S-[2-[(1-Iminoethyl)amino]ethyl]-2-methyl-L-cysteine maleate hydrochloride. FIG. 1, as more fully described below, shows a powder X-ray diffraction pattern (top pattern) of crystal line S-[2-[(1-Iminoethyl)amino]ethyl]-2-methyl-L-cysteine maleate hydrochloride obtained from this example. FIG. 7. shows SEM pictures of the randomly packed agglomerates of the product from this example.

Example 10

In Example 10, 301 mg of 0.13 eq. HCl containing amorphous freeze dried S-[2-[(1-Iminoethyl)amino]ethyl]-2-methyl-L-cysteine (containing approximately 10% water), 317 mg of maleic acid, 1239 mg of DMF and 457 mg of DI water were added to a 12 ml vial equipped with a magnetic stirrer. The suspension was stirred to affect a clear solution. 8 ml of acetonitrile were slowly added in 0.5 ml aliquots. The system was stirred at room temperature for 24 hours to crystallize out. Temperature of the vial was then increased to 55° C. and it was held at this temperature for 48 hours. Photo-microscopy on slurry samples just prior to heating and after 48 hours at the elevated temperature confirmed that the phase conversion to crystalline S-[2-[(1-Iminoethyl)amino]ethyl]-2-methyl-L-cysteine maleate hydrochloride had occurred. The slurry at 55° C. was quickly filtered on a 30 ml fine frit sintered glass funnel and the cake washed with 1 ml of acetonitrile. The solids were air dried for 2 hours. Analytical data on the product confirmed it to be S-[2-[(1-Iminoethyl)amino] ethyl]-2-methyl-L-cysteine maleate hydrochloride. Proton NMR analysis indicated that the product may have trapped DMF at 0.06 moles per mole of S-[2-[(1-Iminoethyl)amino] ethyl]-2-methyl-L-cysteine maleate hydrochloride.

Example 11

In Example 11 313 mg of 0.13 HCl containing amorphous freeze dried S-[2-[(1-Iminoethyl)amino]ethyl]-2-methyl-L-cysteine (containing approximately 10% water), 313 mg of maleic acid, 1247 mg of DMF and 453 mg of DI water were added to a 12 ml vial equipped with a magnetic stirrer. The suspension was stirred to affect a clear solution. 8 ml of acetonitrile were slowly added in 1.0 ml aliquots. Crystallization seemed to have occurred with the addition of 7.5 ml of acetonitrile. The charge was, however completed to 8 ml and the slurry was stirred at room temperature for 24 hours to de-saturate. Temperature of the vial was then increased to 56° C. and it was held at this temperature for 24 hours. Photomicroscopy on slurry samples just prior to heating and after 24 hours at the elevated temperature confirmed that the phase conversion to crystalline S-[2-[(1-Iminoethyl)amino]ethyl]-2-methyl-L-cysteine maleate hydrochloride had occurred. The slurry at 56° C. was quickly filtered on a 30 ml fine frit sintered glass funnel and the cake washed with 1 ml of acetonitrile. The solids were air dried for 2 hours. Analytical data on the product confirmed it to be S-[2-[(1-Iminoethyl)amino] ethyl]-2-methyl-L-cysteine maleate hydrochloride. Proton NMR analysis indicated that DMF was not trapped by the product.

Example 12

Example 12 was performed to determine if S-[2-[(1-Iminoethyl)amino]ethyl]-2-methyl-L-cysteine maleate hydrochloride could be nucleated directly by initiating the crystallization process at an elevated temperature and if the filtration of hot slurry could be avoided. 302 mg of 0.13 eq. HCl containing amorphous freeze dried S-[2-[(1-Iminoethyl) amino]ethyl]-2-methyl-L-cysteine (containing approximately 10% water), 321 mg of maleic acid, 1223 mg of DMF and 453 mg of water were added to a 12 ml vial equipped with a magnetic stirrer. The suspension was heated to 60° C. and stirred to affect a clear solution. 8 ml of acetonitrile were slowly added to the solution at 60° C. in 1 ml aliquots. No crystallization was observed during the addition process, however crystals did form within 20 minutes of the completion of acetonitrile charge. The slurry was stirred at 60° C. for 25 hours. 2 ml of acetonitrile were added to lower the water activity of the system. The slurry was stirred at 60° C. for another 20 hours and then naturally cooled to room temperature and stirred for 2 hours before being filtered on a fine frit sintered glass funnel. The cake was rinsed with 2 ml acetonitrile and air dried for 20 minutes. Analytical data on the product confirmed it to be crystalline S-[2-[(1-Iminoethyl) amino]ethyl]-2-methyl-L-cysteine maleate hydrochloride.

Example 13

Example 13 was conducted in DMF/acetonitrile to simplify the solvent system. The procedure involved adding 202 mg of 0.13 eq. HCl containing amorphous freeze dried S-[2-[(1-Iminoethyl)amino]ethyl]-2-methyl-L-cysteine (containing approximately 10% water), 213 mg of maleic acid and 1139 mg of DMF to a 12 ml vial equipped with a magnetic stirrer. The suspension was heated to 60° C. and stirred to affect a clear solution. 4 ml of acetonitrile were slowly added to the solution at 60° C. in 1 ml aliquots over 20 minutes. Crystals were observed within 20 minutes of the completion of acetonitrile charge. The slurry was stirred for 24 hours at 60° C. and then cooled to 25° C. in forty-five minutes. It was stirred at 25° C. for 2 hours and then filtered on a fine frit sintered glass funnel. The cake was washed with 1 ml of acetonitrile and air dried for twenty minutes. Solids were then dried in a vacuum oven at 40° C. under 28 inches Hg vacuum for 24 hours. Proton NMR analysis on the solids prior to oven drying, however, indicated that there was no trapped DMF in the solids. Oven drying was therefore not necessary. All the analytical data on air-dried and vacuum dried solids from this experiment confirmed the solids to be crystalline S-[2-[(1-Iminoethyl)amino]ethyl]-2-methyl-L-cysteine maleate hydrochloride.

Example 14

In Example 14,311 mg of 0.25 eq. HCl containing amorphous freeze dried S-[2-[(1-Iminoethyl)amino]ethyl]-2-methyl-L-cysteine (containing approximately 10% water), 321 mg of maleic acid, 1231 mg of DMF and 451 mg of DI water were added to a 12 ml vial equipped with a magnetic stirrer. The suspension was stirred to affect a clear solution. 8 ml of acetonitrile were slowly added in 0.5 ml aliquots. It was stirred at room temperature for 24 hours to de-saturate. Temperature of the vial was then increased to 57° C. and stirring continued for another 24 hours. The slurry at 57° C. was quickly filtered on a 30 ml fine frit sintered glass funnel and the cake washed with 1 ml of acetonitrile. The solids were aid dried for thirty minutes and then placed in a vacuum oven at 40° C. and 28 inches Hg vacuum for 24 hours. Analytical data on the product confirmed it to be crystalline S-[2-[(1-Iminoethyl)amino]ethyl]-2-methyl-L-cysteine maleate hydrochloride. Proton NMR analysis indicated that neither the air-dried nor the vacuum dried solids had trapped DMF.

Example 15

Example 15 was conducted in DMF/acetonitrile to simplify the solvent system. The procedure involved adding 608 mg of 0.25 eq. HCl containing amorphous freeze dried S-[2-[(1-Iminoethyl)amino]ethyl]-2-methyl-L-cysteine (containing approximately 10% water), 648 mg of maleic acid and 3320 mg of DMF to a 25 ml vial equipped with a magnetic stirrer. The suspension was stirred to affect a clear solution. 10 ml of acetonitrile were slowly added to the solution in 2 ml aliquots over 20 minutes. Crystals were observed within 20 minutes of the completion of acetonitrile charge and extensive precipitation was observed within 4 hours. The slurry was stirred for 19 hours and then a solid sample was withdrawn for in-process check. Thermal analysis on the sample indicated that it may contain some Form I of S-[2-[(1-Iminoethyl)amino]ethyl]-2-methyl-L-cysteine maleate. The slurry was therefore, heated to 50° C. in order to selectively dissolve the Form I of S-[2-[(1-Iminoethyl)amino]ethyl]-2-methyl-L-cysteine maleate. Solid sample withdrawn thirty minutes after reaching 50° C. indicated that Form I of S-[2-[(1-Iminoethyl)amino]ethyl]-2-methyl-L-cysteine maleate had indeed been eliminated from the desired solids. 4 ml of acetonitrile were added to the slurry at 50° C., two hours after reaching the elevated temperature. The slurry was held at 50° C. for another hour and then cooled to 0° C. in five and a half hours using a linear temperature ramp. It was stirred at 0° C. for forty hours and then filtered on a fine frit sintered glass funnel. Filtration was extremely slow. The cake was washed with 4 ml of acetonitrile and air dried for one hour. The air-dried cake weighed 198 mg. This however, does not reflect the true yield from the process because five in-process solid samples of up to 30 mg each were withdrawn during this experiment. Proton NMR analysis on the air-dried indicated that there was 0.035 molar equivalent of DMF in the solids. Concentration analysis on the mother liquor prior to the cool down to 0° C. and after the nineteen hour hold at this temperature indicated that this operation did not help de-saturate the system any further. This may however, be due to the complete depletion of HCl even before the system was cooled. Analytical data on the product confirmed it to be crystalline S-[2-[(1-Iminoethyl)amino]ethyl]-2-methyl-L-cysteine maleate hydrochloride.

Example 16

Example 16 was performed to optimize acetonitrile volumes, evaluate 25% reduction in the amount of maleic acid (to improve yield) and reduce and rationalize hold times. 304 mg of 0.25 eq. HCl containing amorphous freeze dried S-[2-[(1-Iminoethyl)amino]ethyl]-2-methyl-L-cysteine (containing approximately 10% water), 240 mg of maleic acid and 1662 mg of DMF were added to a 12 ml scintillation vial equipped with a magnetic stirrer. The suspension was stirred to affect a clear solution. 3 ml of acetonitrile were slowly added to the solution in 0.5 ml aliquots over 20 minutes. Crystals were observed within two hours of acetonitrile charge. The vial was stirred for twenty-two hours and then filtered on a fine frit sintered glass funnel. The cake was washed with 2 ml of acetonitrile and air dried for half an hour. Solids were placed in a vacuum oven at 55° C. and 28 inches Hg for 24 hours. Proton NMR analysis on the oven dried solids indicated that there was 0.03 molar equivalent of DMF in the solids. Concentration analysis on the filtrate indicated that this recipe had a molar yield approaching 50%. This may, however, still be suppressed due to the complete depletion of HCl. Analytical data on the product confirmed it to be crystalline S-[2-[(1-Iminoethyl)amino]ethyl]-2-methyl-L-cysteine maleate hydrochloride.

Example 17

The objective of Example 17 was to study the crystallization of S-[2-[(1-Iminoethyl)amino]ethyl]-2-methyl-L-cysteine maleate hydrochloride at 0.63 molar equivalents of HCl (0.13 molar excess). 220 mg of 0.13 eq. HCl containing amorphous freeze dried S-[2-[(1-Iminoethyl)amino]ethyl]-2-methyl-L-cysteine (containing approximately 10% water), 232 mg of maleic acid, 31.98 mg of 37% concentrated HCl (aqueous) and 1164 mg of DMF were added to a 12 ml vial equipped with a magnetic stirrer. The suspension was stirred to affect a clear solution. 3.0 ml of acetonitrile were slowly added to the solution in 0.5 ml aliquots over 25 minutes. Turbidity subsided completely upon the completion of the charge, however some oily residue could be seen on the walls of the vial. The vial was stirred at room temperature for seventeen hours and then filtered on a fine frit sintered glass funnel. The cake was washed with 2 ml of acetonitrile and air dried for half an hour. The cake had compressed very tightly and was difficult to remove from the funnel. Solids were placed in a vacuum oven at 55° C. and 28 inches Hg for 24 hours. Filtrate analysis indicated a molar yield of approximately 75%. Analytical data on the product confirmed it to be crystalline S-[2-[(1-Iminoethyl)amino]ethyl]-2-methyl-L-cysteine maleate hydrochloride.

Example 18

Experiment 18 was performed at 0.63 molar equivalents of HCl (0.13 molar excess) with one mole of butanol for each mole of S-[2-[(1-Iminoethyl)amino]ethyl]-2-methyl-L-cysteine. Spiking with butanol was studied because it can be a potential impurity in the feed S-[2-[(1-Iminoethyl)amino] ethyl]-2-methyl-L-cysteine. 210 mg of 0.13 eq. HCl containing amorphous freeze dried S-[2-[(1-Iminoethyl)amino] ethyl]-2-methyl-L-cysteine (containing approximately 10% water), 232 mg of maleic acid, 72 mg of butanol, 36.0 mg of 37% concentrated HCl (aqueous) and 1186 mg of DMF were added to a 12 ml vial equipped with a magnetic stirrer. The suspension was stirred to affect a clear solution. 3.0 ml of acetonitrile were slowly added to the solution in 0.5 ml aliquots over 25 minutes. The vial was stirred at room temperature for seventeen hours and then filtered on a fine frit sintered glass funnel. The cake was washed with 2 ml of acetonitrile and air dried for half an hour. Solids were placed in a vacuum oven at 55° C. and 28 inches Hg for 24 hours. Filtrate analysis indicated a molar yield of approximately 60%. Analytical data on the product from this experiment confirmed formation of crystalline S-[2-[(1-Iminoethyl)amino]ethyl]-2-methyl-L-cysteine maleate hydrochloride and indicated that the presence of butanol does not lead to any adverse affect on crystal quality. The yield for the process is, however, lowered.

Experiment 19

Experiment 19 was performed at 0.88 molar equivalents of HCl (0.33 molar excess). 221 mg of 0.13 eq. HCl containing amorphous freeze dried S-[2-[(1-Iminoethyl)amino]ethyl]-2-methyl-L-cysteine (containing approximately 10% water), 233 mg of maleic acid, 54.0 mg of 37% concentrated HCl (aqueous) and 1196 mg of DMF were added to a 12 ml vial equipped with a magnetic stirrer. The suspension was stirred to affect a clear solution. 3.0 ml of acetonitrile were slowly added to the solution in 0.5 ml aliquots over 25 minutes. Turbidity subsided completely upon the completion of the charge, however some oily residue could be seen on the walls of the vial. The vial was stirred at room temperature for seventeen hours and then filtered on a fine frit sintered glass funnel. The cake was washed with 2 ml of acetonitrile and air dried for half an hour. The cake had compressed very tightly and was difficult to remove from the funnel. Solids were placed in a vacuum oven at 55° C. and 28 inches Hg for 24 hours.

Filtrate analysis indicated a molar yield of approximately 58%, which is significantly lower than the 75% observed in experiments where HCl concentration was closer to the stoichiometric. It therefore seems that both the excess and deficiency of HCl in the system tend to lower the yields. Analytical data on the product from this experiment confirmed formation of crystalline S-[2-[(1-Iminoethyl)amino]ethyl]-2-methyl-L-cysteine maleate hydrochloride.

Discussion of Randomly Packed Agglomerate Examples

While Examples 10 through 19, demonstrate that S-[2-[(1-Iminoethyl)amino]ethyl]-2-methyl-L-cysteine maleate hydrochloride could be crystallized under conditions representing severe deficiency or excess of HCl in relation to S-[2-[(1-Iminoethyl)amino]ethyl]-2-methyl-L-cysteine, all of these examples represent sub-optimal conditions for the crystallization of S-[2-[(1-Iminoethyl)amino]ethyl]-2-methyl-L-cysteine maleate hydrochloride. This discussion would therefore be limited to the more optimal procedures for crystallization of S-[2-[(1-Iminoethyl)amino]ethyl]-2-methyl-L-cysteine maleate hydrochloride that are best captured by Examples 7 through 9.

Examples 7 and 8 only differ in the nature of agitation afforded to the system. The former employed an overhead motor connected to a shaft and a "half moon" blade that does not touch any surface of the crystallization flask, while the latter used a magnetic bead in contact with the bottom surface of the crystallization flask. The bead was agitated with a magnetic plate. This variable was studied in these examples to demonstrate that the randomly packed agglomerated shape obtained in example 8 was not confounded by the use of magnetic bead, which had shown the propensity of converting orderly packed agglomerates to randomly packed agglomerates upon extended hold periods (see Example 26). Both the examples used 2.0 molar equivalents of maleic acid and 0.5 molar equivalent of HCl for each mole of S-[2-[(1-Iminoethyl)amino]ethyl]-2-methyl-L-cysteine. The water content of the system was held at 1.63% (measured before the addition of acetonitrile), while the ratio of acetonitrile to DMF was 1.4 on weight/weight basis. In Example 9, the water content of the system was 2.3% before the addition of acetonitrile, while the ratio of acetonitrile to DMF was 1.98 on weight/weight basis. Both S-[2-[(1-Iminoethyl)amino]ethyl]-2-methyl-L-cysteine and S-[2-[(1-Iminoethyl)amino]ethyl]-2-methyl-L-cysteine maleate hydrochloride are highly soluble in water and therefore the use of extra water in Example 9 allowed the acetonitrile to DMF ratio to be increased to 1.98, without even more significant crystallization during the addition of acetonitrile.

These three experiments are characterized by: a) fast nucleation and significant crystallization of S-[2-[(1-Iminoethyl) amino]ethyl]-2-methyl-L-cysteine maleate hydrochloride during the acetonitrile addition resulting in rapid de-saturation of the system; b) accelerated growth of the fastest growing crystal face resulting in larger aspect ratios; and c) no visual or other indication of sustained phase separation during or upon completion of acetonitrile charge. Detailed definition, discussion and significance of phase separation would be deferred to the next sub-section on the discussion of QESD crystallization technique. For the purpose of this discussion, it is sufficient to say that the lack of phase separation also contributes to the fast crystallization observed in these three examples.

In the absence of phase separation, fast crystallization leads to either the formation of very small needle-like crystals, if most of the de-saturation occurs through nucleation from a solution, or slightly elongated needle like crystals if more de-saturation occurs through rapid crystal growth along the long crystal dimension. Either scenario can lead to randomly packed agglomerates through compaction of cake during filtration or even in the crystallization flask if high agitation is afforded (for instance an rpm greater than 350 in Example 7).

DETAILED DEFINITION OF PHASE SEPARATION

For the purpose of this invention, phase separation is defined as any state of the crystallization system comprising of more than one liquid phase and or solids that are not crystalline. These non-crystalline solids could resemble a visually observable sticky mass usually but not necessarily completely amorphous, while the second liquid phase could resemble visually and or microscopically observable emulsion, visually and or microscopically unobservable emulsion (for instance due to improper sampling), visually and or microscopically observable "oily coating" on the surfaces including crystals in the crystallization flask and visually and or microscopically unobservable "oily coating" (for instance due to the lack of thickness) on the surfaces including crystals in the crystallization flask.

Phase separation seems to be a manifestation of the "emulsifying agent like" nature of S-[2-[(1-Iminoethyl)amino]ethyl]-2-methyl-L-cysteine in the crystallization system comprising DMF, acetonitrile, water, maleic acid and HCl. It occurs when a certain concentration of S-[2-[(1-Iminoethyl)amino]ethyl]-2-methyl-L-cysteine at a specific water content, maleic acid and HCl strength in a solution of given DMF-acetonitrile composition is achieved prior to or during precipitation of S-[2-[(1-Iminoethyl)amino]ethyl]-2-methyl-L-cysteine maleate hydrochloride. The extent of phase separation is a strong function of all these intrinsic process parameters, in addition to variables such as the strength of agitation, available surfaces and addition rate of the acetonitrile.

By definition when binary phase separation occurs, two phases with different compositions are formed. For the S-[2-[(1-Iminoethyl)amino]ethyl]-2-methyl-L-cysteine/maleic acid/HCl/water/DMF/acetonitrile system, when a visually or microscopically observable classic emulsion results from the phase separation process, the continuous phase becomes the rare phase with higher acetonitrile percentage and lower S-[2-[(1-Iminoethyl)amino]ethyl]-2-methyl-L-cysteine concentration than the original single phase solution. Conversely, the non-continuous dispersed phase becomes the dense phase with lower acetonitrile percentage and higher S-[2-[(1-Iminoethyl)amino]ethyl]-2-methyl-L-cysteine concentration than either the continuous rare phase or the original single phase solution. When instead a visually or microscopically observable "oily coating" results from the phase separation process, complete analysis of the two phases becomes difficult. Analysis of the continuous phase, however, does show a higher acetonitrile percentage and lower S-[2-[(1-Iminoethyl)amino]ethyl]-2-methyl-L-cysteine concentration than the original single phase solution. In fact, these characteristics of the phases could be used as the analytical test to determine the onset of the formation of stable phase separated system, especially under conditions where classic emulsion or observable "oily coating" may be difficult to detect visually or microscopically.

Theoretical Crystallization Models

While theory plays no part in the instant invention, the following mechanisms are described to better acquaint those skilled in the art with the processes of the present invention.

QESD Based Crystallization

Binary solvent mixtures used in QESD based crystallization process are characterized by unfavorable interactions (de-mixing) between the solvent and anti-solvent. Typical solvent combinations include water-acetone, water-acetonitrile, ethanol-cyclohexane and water-ethyl acetate.

The solvent tends to have very high solubility for the solute, while the anti-solvent is often characterized by negligible solubility for the solute. Solubility of the solute in the solvent as high as 1.92 g/g has been reported. Solvents with high solubility are in fact selected to maximize the strength of interactions between solute and solvent. An emulsifying agent (a surfactant) is usually dissolved in the anti-solvent to facilitate the emulsification process. Anti-solvent to solvent ratios can be as high as 50 to 1.

The process starts by dissolving the solute in solvent and adding this solution to a solution of anti-solvent and emulsifying agent at a controlled rate. Often a temperature difference is also maintained between the solvent and anti-solvent solutions, with the latter being at a lower temperature. Upon the addition of the solvent solution, a stable emulsion is created, where the solvent solution is the dispersed phase and the anti-solvent solution is the continuous phase. Super-saturation is created through heat transfer (temperature difference) and more importantly mass transfer (counter diffusion of solvent and anti-solvent out of and into the droplets of the dispersed phase). The dispersed phase de-saturates through crystallization in the dispersed phase. At the harvest point, there is only one liquid phase formed through the counter-diffusion mass transfer process described which has been described.

In QESD crystallization processes, only a fraction of the solute precipitates out due to the mild super-saturation created by the often but not always used temperature differential, which is maintained during the early phases of the process between the solvent and anti-solvent solutions. In other words, the initial super-saturation created by temperature differential is only moderate (maximum reported initial super-saturation in the literature is ~40%) and even as counter-diffusion of anti-solvent and solvent commences, the rate of super-saturation generation is slow because of the slow transfer across the droplet boundary. Consequently, such processes operate under relatively mild residual super-saturation for much of the duration and are therefore characterized by slow overall de-saturation rates. Another common feature of such processes is that the concentration of the solute in the continuous phase actually increases, albeit only slightly, as the solubility of the solute increases in the anti-solvent rich phase through diffusion of the solvent from the dispersed phase.

High Super-Saturated Induced LLPS Based Crystallization

There is growing evidence that super-saturated solutions, especially those of protein, protein like molecules and systems that make colloidal solutions can undergo a further super-saturation induced separation into two meta-stable "non-equilibrium" liquid phases of different compositions. The on-set of phase-separation or de-mixing on cursory inspection resemble typical cloud point for a crystallization process, however, techniques such as microscopy readily indicate that the turbidity is not due to the formation of crystalline solids. The de-mixing process inherently creates an even more super-saturated phase coexisting with a less super-saturated or even under-saturated phase. Crystallization initially commences in the higher super-saturation phase, which can for certain conditions resemble a typical dispersed phase in an emulsion or a quasi-emulsion of the type described in the preceding section. Agglomerate-like morphologies similar to those shown in FIG. 8 have also been reported for processes based on high super saturation induced LLPS.

Both binary and single solvent systems exhibiting LLPS type behavior are known. In all cases, the solubility of the solute in the solvent system of choice is moderate (numbers at high end are no greater than 200 mg/gram), which is in sharp contrast to the solvent solutions used in QESD type design.

A significant body of literature exists on the solution properties of the systems that exhibit LLPS under super-saturated conditions. In addition to typical transitions such as solidification below the liquidus, phase diagrams also exhibit an atypical liquid-liquid phase separation, also referred to as coacervation, wherein the meta-stable solution forms two distinct non-equilibrium liquid phases with unequal concentrations of the solute. The co-existence curve on the diagram represents the concentration of coexisting solute rich and solute poor liquid phases as a progressively more super-saturated solution of the solute is created by continuing to move vertically downward from the liquidus line.

Experimental techniques to establish the co-existence curve include two very simple procedures; cloud point and temperature quench methods. Briefly, with the former, the opacification temperature is determined for each fixed solute concentration, while with the latter the super-saturated solution is cooled to a fixed temperature below the phase separation temperature and then the two co-existing phases are analyzed for concentration For binary systems (solute and single solvent), the maximum temperature on the co-existence curve is called the critical temperature of phase separation and the corresponding concentration is called the critical concentration.

Critical concentration plays a pivotal role in establishing the "morphology" of the two phases. In systems with concentration less than the critical concentration, nucleation and growth of spherical, uniformly sized droplets containing the solute rich phase is observed. In systems with concentration greater than the critical concentration, again nucleation and growth of spherical, uniformly sized droplets is often observed. In this case, however, the droplets contain the solute poor phase. In extreme cases, instead of phase separation, gelation could also be observed as the temperature is lowered below the liquidus line. Crystalline domains can often be observed as this gel phase (usually amorphous solids) containing system is cooled to temperatures below the co-existence curve. In systems with concentration very close to critical concentration, two inter-connected domains appear.

Figure 10:
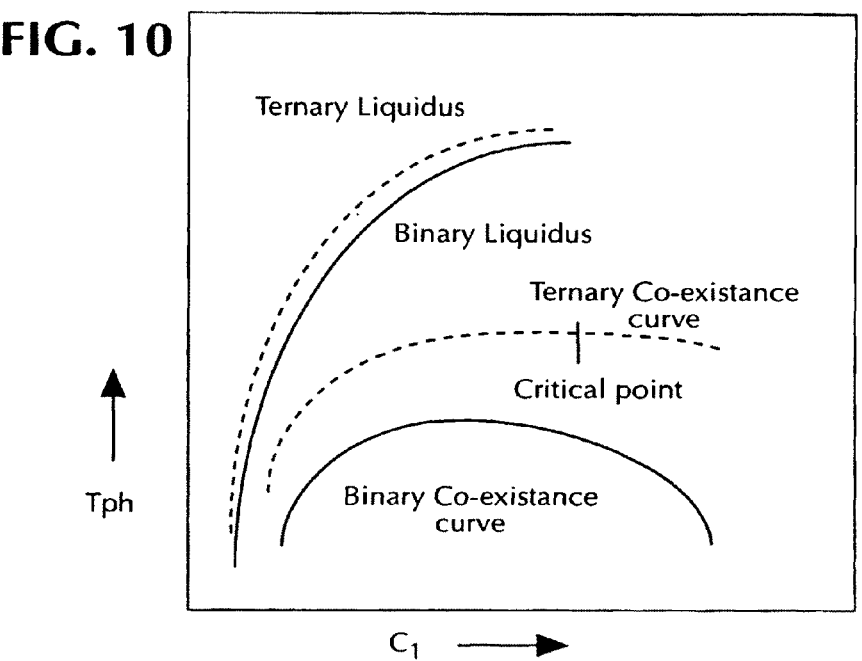
FIG. 10 is a conceptual x-T diagram for a ternary system exhibiting LLPS behavior for a fixed amount of anti-solvent

For a ternary system comprising solute, solvent and anti-solvent, the co-existence surface (see FIG. 10) represents LLPS temperature as a function of solute $c_1$ for a fixed amount of anti-solvent at concentration $c_2$. At a fixed temperature, the LLPS properties of the system are described by an isothermal coexistence curve (see FIG. 11), which gives the concentrations $(c_1, c_2)^I$ and $(c_1, c_2)^{II}$ in the two coexisting phases I and II generated by starting with solutions of different solute concentration for a fixed amount of anti-solvent. The partitioning of the two phases can be best captured by the tie lines connecting the points I and II on the coexisting curve drawn at constant temperature (see FIG. 11). For a ternary system, the critical point $(c_1, c_2)^c$ is defined as the point on coexistence plot where the condition $(c_1, c_2)^I$ equal $(c_1, c_2)^{II}$ is satisfied. The location of this point as a function of temperature is described as the critical line on the co-existence surface. As shown in FIG. 10, the net effect of adding a fixed amount of anti-solvent or precipitating agent (such as polyethylene glycol) to a solute-solvent solution is the upward shift of the entire coexistence curve towards the liquidus (which may itself move upward but not to the same extent as the upward move of co-existence curve), in addition to some distortion in the symmetry of the shape of the curve itself. The latter has consequences for the composition of two phases and their relative fractions.

As more precipitating agent or a stronger precipitating agent is introduced in the solute solvent solution, the shifts become more pronounced and the curve more asymmetric. The net effect of these shifts is that the gap between the liquidus and coexistence curve reduces as LLPS temperature increases and consequently, LLPS occurs at even lower super-saturations. Critical point moving to lower concentrations of the solute due to the asymmetry has implications for the morphology of the phase separated liquid phases.

Figure 11:
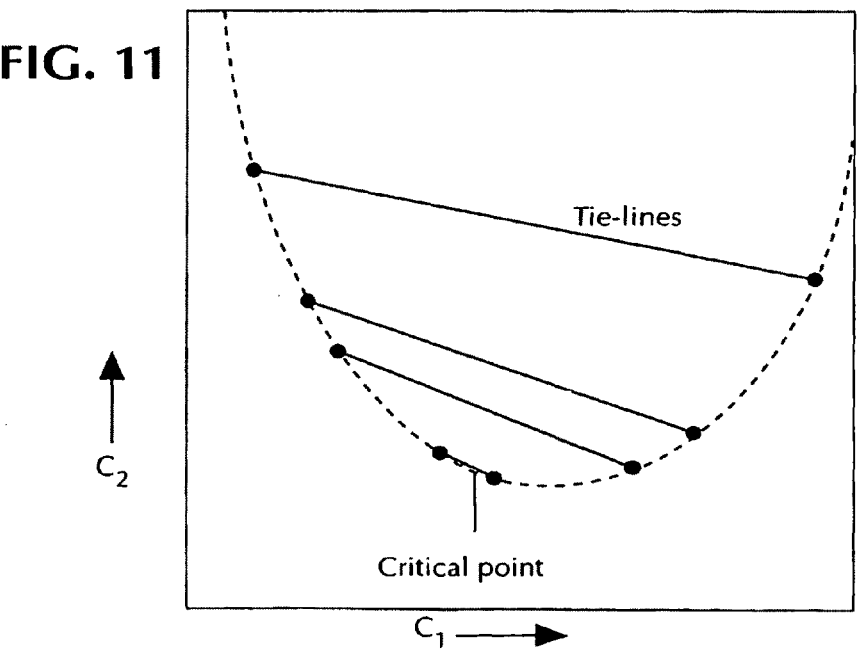
FIG. 11 is a chart showing coexisting surfaces at constant temperature for a ternary system

The slope of LLPS temperature as a function of anti-solvent concentration at the critical point, the critical temperature and the concentration of the anti-solvent can actually be used to calculate the LLPS temperature in the absence of the anti-solvent by the mathematical model developed in reference 15. This is extremely attractive when LLPS of a solute solvent system is not accessible due to either freezing of the system or crystallization of solute prior to reaching the LLPS temperature or super-saturation. Furthermore, the slope of the tie lines in FIG. 11 is proportion to the fractional decrease in solute solubility due to the presence of a given concentration of the anti-solvent or the precipitating agent. In other words, the slope of tie lines characterizes the effectiveness of a solute-precipitating agent such as the anti-solvent. Consequently, this information can be used to predict the liquidus lines in the presence of the anti-solvent.

The effect of a second solute (such as structurally related impurities) similar to the primary solute is usually limited to vertical displacement (usually downwards i.e., decrease in LLPS temperature) of the coexistence curve along the temperature axis for the binary system[18]. During these displacements the curve retains its shape, unlike the situation encountered in the presence of a precipitating agent or an anti-solvent. However, if the second solute or the impurity is dissimilar to the primary solute, then in addition to vertical displacement (again usually downwards) along the temperature axis, the shape of the coexistence curve is also distorted. The curves become increasingly asymmetric, with the critical points shifting to higher primary solute concentrations, while at the same time the maximum LLPS temperature shifting to lower primary solute concentrations. It seems that the net effect of a second solute is that more super-saturation is needed to observe LLPS in ternary systems containing a second solute phase such as an impurity.

In the context of LLPS based design, the dissimilarity between solute species is best captured by identifying the differences in the critical point for each species in a binary system comprising of that solute and a solvent common to all the species under investigation. The asymmetry caused in the coexistence curve by the presence of dissimilar second solutes such as impurities, again has consequences for the relative fraction and morphology of the two liquid phases obtained upon LLPS.

Cycling through the LLPS surface can significantly reduce induction times to nucleation well above the LLPS temperatures (>2.0° C.). Nucleation rate increases in excess of six folds have been reported at temperatures greater than LLPS temperatures by 1-1.5° C. Two reasons have been postulated for this significant increase in nucleation rate. First is the reduction in the $\Delta G_{nuc}$ because the system approaches the spinodal just above the bi-nodal at LLPS temperature. In the spinodal region density fluctuations are higher than at any other point in the vicinity and this in turn leads to reduction in $\Delta G_{nuc}$. Furthermore, the number of molecules needed to make a stable pre-nucleation cluster drops significantly, because of the reduction in $\Delta G_{nuc}$. Second, in the approach to LLPS temperature, phenomenon akin to wetting of the crystal nuclei surfaces by high solute concentration liquid can also enhance nucleation rate. The nucleation rate reduces back to that predicted by classical nucleation rate expressions as the system enters the LLPS regime. The rates can be estimated with some accuracy from the respective super-saturations in the solute rich and solute poor phases by using appropriate classical nucleation models.

Crystal morphology obtained through crystallization under the LLPS surface seems to be related to the onset single-phase solute concentration in relation to the critical point. This is in turn related to the actual "morphology" of the solute rich and solute poor liquid phases on either side of the critical point. As described earlier, in systems with concentration less than the critical concentration, nucleation and growth of spherical, uniformly sized droplets containing the solute rich phase is observed. Crystallization commences in the highly super-saturated solute-rich droplet through multiple nucleations at the core of the droplet thereby transforming it into polycrystalline solid phase. New crystals form and grow radially outwards from the poly-crystalline core and consume not only the remaining solute in the droplet but also the solute in solute-poor phase, which cannot usually precipitate on its own because of the low super-saturation in the solute-poor continuous phase.

In systems with concentration greater than the critical concentration, again nucleation and growth of spherical, uniformly sized droplets is often observed. In this case, however, the droplets contain the solute poor phase. Irregular polycrystalline solids with very small primary particles are obtained for these systems. However, if the concentration is significantly higher than the critical concentration, gelation (due to the formation of amorphous solids) might be observed even before LLPS temperature is approached. When such a system is brought below the LLPS curve, crystals form within the gel matrix. The rate of transformation of a gel phase containing system to a totally crystalline material is however, significantly slower than a corresponding system that contains high concentration liquid droplets instead. The reason for slow transformation in the gel phase it related to the fact the mobility is arrested due to the formation of the gel, which in turn retards the crystal nucleation rate.

Figure 8:
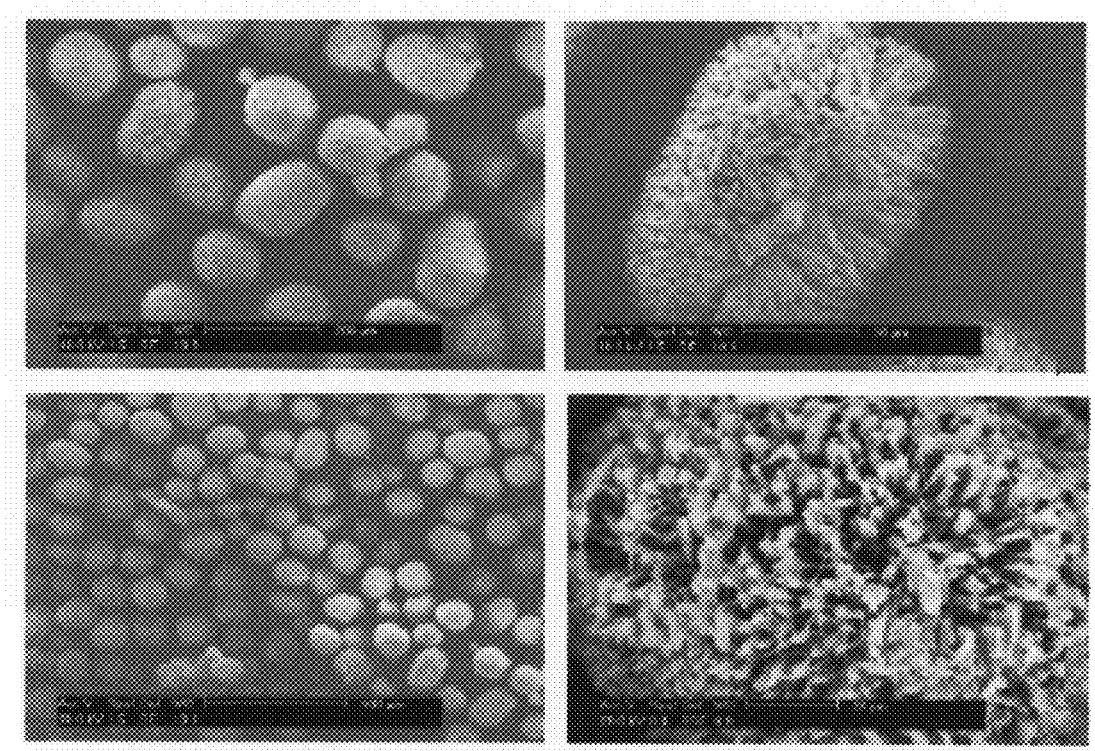
FIG. 8 shows various SEM pictures of the orderly packed agglomerates of crystalline S-[2-[(1-Iminoethyl)amino]ethyl]-2-methyl-L-cysteine maleate hydrochloride made through seeded QESD crystallization process and obtained from Example 20.

In summary LLPS based crystallization processes operating below the co-existence curve and to the left of the critical point can produce morphologies similar to those observed for crystalline S-[2-[(1-Iminoethyl)amino]ethyl]-2-methyl-L-cysteine maleate hydrochloride (see FIG. 8). In such processes the super-saturation in the solute-rich dispersed phase is usually very high. Also analysis of solute concentration in the solute-poor continuous phase show a continual decrease as the overall system crystallizes out. In conclusion, basic observations and data, all the crystallization process characterization data and observed crystal morphology are congruent with the general features of an LLPS based crystallization process operating just below the co-existence curve and to the left of the critical point. This conceptual design is therefore proposed as the model to describe the crystallization of S-[2-[(1-Iminoethyl)amino]ethyl]-2-methyl-L-cysteine maleate hydrochloride as orderly packed spherical agglomerates.

All three designs for a crystallization process for S-[2-[(1-Iminoethyl)amino]ethyl]-2-methyl-L-cysteine maleate hydrochloride to produce orderly packed agglomerates take the procedures reported in Examples 7 through 9 for the randomly packed agglomerates as the starting points. Major modifications include changes in the level of maleic acid, water content and acetonitrile to DMF ratio. The ratio of acetonitrile to DMF on weight/weight basis is relaxed from either 1.4 or 1.8 to whatever is necessary to achieve phase separation prior to or during early stages of the precipitation of S-[2-[(1-Iminoethyl)amino]ethyl]-2-methyl-L-cysteine maleate hydrochloride crystals. Maleic acid molar equivalents in relation to S-[2-[(1-Iminoethyl)amino]ethyl]-2-methyl-L-cysteine is increased to at least 2.2 from 2.0 and water content of the system prior to the addition of acetonitrile is at least 2.83% on weight basis. Increase in the levels of maleic acid and water enhances the solubility of S-[2-[(1-Iminoethyl)amino]ethyl]-2-methyl-L-cysteine in the solvent solution and therefore helps ensure that the concentration of S-[2-[(1-Iminoethyl)amino]ethyl]-2-methyl-L-cysteine at a specific water content, maleic acid and HCl strength in a solution of given DMF-acetonitrile composition does not drop below a specific level needed for phase separation manifested either as visually or microscopically emulsion or visually or microscopically observable or even unobservable "oily coating" of surfaces including those offered by the small number of crystals that might form during the addition of anti-solvent. All three designs involve addition of the anti-solvent solution to the solvent solution and are performed at relatively mild levels of agitation.

In externally seeded crystallization process for S-[2-[(1-Iminoethyl)amino]ethyl]-2-methyl-L-cysteine maleate hydrochloride, anti-solvent solution (acetonitrile) is added to solvent solution (best described by the secondary DMF solution of S-[2-[(1-Iminoethyl)amino]ethyl]-2-methyl-L-cysteine solution as defined earlier) in a controlled manner such that the total addition time is preferably in excess of about thirty minutes and more preferable still, about ninety minutes. Addition of the anti-solvent solution can be continuous, for instance using a pump at a specific addition rate, or preferably intermittently where a small aliquot of the total anti-solvent solution volume is added at given time intervals. These intervals are optimal when the duration between successive aliquot additions is long enough to ensure that most of the turbidity (manifestation of unstable phase separation) that forms immediately upon the addition of an aliquot has had adequate time to subside. The anti-solvent solution is added until the turbidity that results from the addition of each aliquot either does not completely subside or subsides but leaves behind a very fine oily coating only visible on surfaces such as the agitation shaft, agitation blade, walls of the reactor or baffles in the crystallization flask. At this point a very small amount of seed crystals is added to the system. Seed crystals are preferably very small crystals of S-[2-[(1-Iminoethyl)amino]ethyl]-2-methyl-L-cysteine maleate hydrochloride, such as those made in Examples 7 through 9. No more than 1% of these seed crystals on weight basis of the original mass of S-[2-[(1-Iminoethyl)amino]ethyl]-2-methyl-L-cysteine dissolved in the solvent solution are usually needed for the purpose of successful externally seeded crystallization process. Seed crystals act as substrate for non-continuous phase that manifests itself either as an emulsion or oily coating. The process is often very slow and takes more than forty-eight hours before the system is completely de-saturated. The process can, however be accelerated, for instance, by increasing the amount of seeding. Orderly packed agglomerates obtained from this type of externally seeded crystallization process are often spherical in shape and are very similar in size.

Seed crystals can also be created in-situ during the anti-solvent solution addition. These crystals can then act as substrate for the non-continuous phase that manifests itself either as an emulsion or oily coating upon phase separation. Nucleation of seed crystals can be promoted in the mixture of solvent and anti-solvent prior to phase separation, for instance by slightly reducing the water content of the solvent solution or slightly reducing the amount of maleic acid or preferably by altering the rate of super-saturation generation, while keeping everything else the same as for externally seeded crystallization process. The latter, could for instance be achieved by altering the rate of addition for the anti-solvent solution. Modifications to the thermal history of solvent and anti-solvent solutions could also be used as alter the kinetics of crystallization, without changing the overall composition of the system. The main advantage of the in-situ seeded crystallization stems from the fact that seed crystals need not be added externally and their addition need not be so tightly linked to observable phase separation as is the case in the externally seeded crystallization process. Added complexity emanates from the fact that de-saturation of the system caused through the formation of seed crystals must be controlled at levels low enough to ensure that the residual concentration of S-[2-[(1-Iminoethyl)amino]ethyl]-2-methyl-L-cysteine in a mixture of solvent and anti-solvent solutions of a given composition does not fall below the level needed for phase separation manifested either as visually or microscopically emulsion or visually or microscopically observable or even unobservable "oily coating" of surfaces. Furthermore, for an optimum design of in-situ seeded crystallization, it would be preferable if the in-situ seed crystals were small in size or had low aspect ratios. This helps ensure that the final shape of orderly packed agglomerate, which to a certain degree resembles the shape of the substrate seed crystals is similar to that obtained in externally seeded crystallization process where small crystals are used as seeds. At a more practical level, this preference for small size or short low aspect ratio in-situ seeds necessitates that the low extent of de-saturation mentioned earlier be achieved through primarily crystal nucleation process as opposed to crystal growth of fewer nuclei to large sizes. The latter can lead to the formation of large needle like seed crystals, which upon coating with the non-continuous phase and subsequent counter-diffusion controlled crystallization to form orderly packed agglomerates could lead to overall shapes that are more elongated as opposed to spherical. Directing low levels of de-saturation primarily through nucleation of large number of small crystals is however, difficult for S-[2-[(1-Iminoethyl)amino]ethyl]-2-methyl-L-cysteine maleate hydrochloride crystallization. Consequently, it is likely that overall shapes dissimilar to spheres would be obtained from an in-situ seeded crystallization process for S-[2-[(1-Iminoethyl)amino]ethyl]-2-methyl-L-cysteine maleate hydrochloride. Depending on the extent of de-saturation and the resulting substrate surface, the overall crystallization times for in-situ seeded crystallization process can be significantly shorter than the externally seeded QESD crystallization process. Since both the in-situ seeded and externally seeded crystallization processes provide ample crystals as surfaces for coating with the non-continuous phase, the possibility of crystallizing S-[2-[(1-Iminoethyl)amino]ethyl]-2-methyl-L-cysteine maleate hydrochloride as scale on the walls and other surfaces in the crystallization flask through solidification of non-continuous phase adhering to them is significantly reduced by the reduction in the fraction of non-continuous phase available to coat these non-crystalline surfaces.

The final design approach to crystallization for S-[2-[(1-Iminoethyl)amino]ethyl]-2-methyl-L-cysteine maleate hydrochloride crystals as orderly packed agglomerates is to eliminate crystalline substrate (seeds) prior to, during or after phase separation. In addition to ensuring that no crystallization takes place during the mixing of solvent and anti-solvent solutions, a microscopically or preferably visually observable emulsion is generated. This must happen even if oily coating is observed prior to achieving the emulsified state. The simplest approach to obtain a visually observable emulsion for the S-[2-[(1-Iminoethyl)amino]ethyl]-2-methyl-L-cysteine maleate hydrochloride system is to further increase the ratio of acetonitrile to DMF. Acetonitrile levels in excess of 110% (by weight) of the amount of acetonitrile used in either the externally seeded or in-situ seeded crystallization processes described above have proven to be adequate to obtain a visually observable emulsion. Such a state, however, often accompanies oily coating on the walls of the crystallization flask and other external surfaces such as the agitator shaft, blades and baffles (if present). While orderly packed agglomerates, spherical in overall shape can be obtained from the slurry of such a crystallization process after at least 48 hours, the oily coating on walls of the crystallization flask usually crystallizes as scale on the walls that resembles randomly packed agglomerates. If the slurry is not carefully withdrawn from the crystallization flask, both randomly packed and orderly packed agglomerates could be seen in the product. The extent of scaling seems to be related to, among other variables, the amount of extra acetonitrile used to generate a visually observable emulsion.

In summary, all three design approaches to crystallization are capable of producing orderly packed agglomerates. The differences lay in the quality of the agglomerates and also the ease of operability and controllability. Based on these three factors, externally seeded crystallization approach is preferable. Examples demonstrating all three approaches follow.

Examples of Orderly Packed Agglomerates

Examples 20, 21 and 22 represent the externally seeded crystallization system described in the preceding section, while Examples 23 and 24 represent the in-situ seeded crystallization system and Example 25 demonstrates a non-seeded crystallization process. Example 26, demonstrates that orderly packed agglomerates could be destroyed under certain agitation conditions. Solids after such an operation have many features characteristic of the randomly packed agglomerates.

Example 20

In Example 20, 54 grams of amorphous freeze dried S-[2-[(1-Iminoethyl)amino]ethyl]-2-methyl-L-cysteine (containing approximately 10% water), 57.5 grams of maleic acid, 287 grams of DMF and 10.1 grams of 37% concentrated HCl (aqueous) were added to a 1.2 liter jacketed reactor. S-[2-[(1-Iminoethyl)amino]ethyl]-2-methyl-L-cysteine turned into a thick sticky mass upon stirring at 350 rpm and took 1 hour to dissolve, despite good solubility in the solvent system. 750 ml of acetonitrile were added to the clear solution in 20 ml aliquots over forty-five minutes. With the addition of 710 ml, the solution became turbid and remained so; the acetonitrile charge was completed nonetheless. One hour after the completion of charge, most of the turbidity had subsided, however, an oily residue had formed on the walls of the reactor. 1 gram of 37% concentrated HCl (aqueous) was added to the reactor to help dissolve the oil. This addition did not succeed in reducing the extent of oiling out and therefore 27.2 grams of DMF were added to the reactor to increase the solubility of the system. Almost all the oily residue on the walls, re-dissolved within fifteen minutes of the second DMF addition. The solution was stirred overnight at 350 rpm. During the hold period it did not crystallize and therefore 400 mg of seed crystals (that is, crystalline S-[2-[(1-Iminoethyl)amino]ethyl]-2-methyl-L-cysteine maleate hydrochloride) were used to induce nucleation. The system was stirred for another 48 hours and then the slurry was discharged in 300 ml aliquots on a 350 ml fine frit sintered glass funnel.

Filtration was extremely fast. The cake was rinsed with 100 ml of acetonitrile and air dried for one hour. It weighed 46.64 grams. The solids were placed in a vacuum oven at 50° C. and 28 inches Hg vacuum for 24 hours. Oven dried solids weighed 42.96 grams.

This represented approximately 89% recovery on weight basis and 65% on molar basis. Concentration analysis for the zwitterion and HCl on the filtrate helped close the mass balance and verify that HCl was stoichiometric throughout the crystallization. FIG. 8 shows various SEM pictures of the product. It is quite evident from FIG. 8 that this experiment produced an almost mono-dispersed population of orderly packed agglomerates, spherical in shape. FIG. 1 shows PXRD comparison of the solids made in this example and the randomly packed agglomerates reported earlier. The upper powder x-ray diffraction pattern is from Example 9, while the lower powder x-ray diffraction pattern is from Example 20. It seems that the shape differences between the two solids do not have any bearing on the peak shape or intensity. Table 1 summarizes analytical data on the product from this example. FIG. 5 shows the Raman spectrum of the crystalline S-[2-[(1-Iminoethyl)amino]ethyl]-2-methyl-L-cysteine maleate hydrochloride obtained from a sample from Example 20.

Example 21

The objective of Example 21 was to rationalize DMF and HCl addition protocols and identify better mixing conditions for dissolving S-[2-[(1-Iminoethyl)amino]ethyl]-2-methyl-L-cysteine during the early stages of the process.

45.78 grams of maleic acid, 251 grams of DMF and 8.82 grams of 37% concentrated HCl (aqueous) were added to a 1.2 liter jacketed reactor. The system was stirred at 275 rpm to affect a clear solution. 43.3 grams of amorphous freeze dried S-[2-[(1-Iminoethyl)amino]ethyl]-2-methyl-L-cysteine (containing approximately 10% water) were then added to the reactor and it was stirred at 50 rpm for two hours to completely dissolve all the solids. Agitation was increased back to 275 rpm and 612 ml of acetonitrile were added to the solution in 15 ml aliquots over ninety minutes. The solution remained almost clear upon the completion of the acetonitrile charge. 429 mg of seed crystals (that is, crystalline S-[2-[(1-Iminoethyl)amino]ethyl]-2-methyl-L-cysteine maleate hydrochloride) were added to the solution and it was stirred for 45 hours. The slurry was discharged in 200 ml aliquots on a 350 ml fine frit sintered glass funnel.

Filtration was extremely fast. The cake was rinsed with 60 ml of acetonitrile and air dried for one and a half hours. It weighed 36.50 grams. The solids were placed in a vacuum oven at 50° C. and 28 inches Hg vacuum for 24 hours. Oven dried solids weighed 36.42 grams. This represented approximately 94% recovery on weight basis and 70% on molar basis. Concentration analysis for the zwitterion and HCl on the filtrate helped close the mass balance and verify that HCl was stoichiometric throughout the crystallization. Overall shape of the crystals was the same as seen in Example 20. Table 1 summarizes analytical data on the product from this example.

Example 22

The objective of Example 22 was to establish the upper limit on the equivalents of HCl that the system could tolerate without losing control over the formation of orderly packed agglomerates. The total HCl content of the system was approximately 0.73 molar equivalents as opposed to the typical 0.5 molar equivalents.

55.97 grams of maleic acid, 307 grams of DMF and 10.78 grams of 37% concentrated HCl (aqueous) were added to a 1.2 liter jacketed reactor. The system was stirred at 275 rpm to affect a clear solution. Agitation was reduced to 50 rpm and then 52.2 grams of 0.23 eq. HCl containing amorphous freeze dried S-[2-[(1-Iminoethyl)amino]ethyl]-2-methyl-L-cysteine (containing approximately 10% water) were added to the reactor. All the S-[2-[(1-Iminoethyl)amino]ethyl]-2-methyl-L-cysteine dissolved within 20 minutes and the stirrer speed was increased back to 275 rpm. Of the 750 ml of acetonitrile to be added, 695 ml were added in 20 ml aliquots over ninety minutes before the solution turned turbid to the point where turbidity would not readily subside. Upon agitation for one hour, turbidity reduced, but a brown oily residue formed at the bottom of the reactor. 10.2 grams of DMF were added to the reactor to dissolve the oily residue and then the system was seeded with 533 mg of seed crystals (that is, crystalline S-[2-[(1-Iminoethyl)amino]ethyl]-2-methyl-L-cysteine maleate hydrochloride). It was stirred for 24 hours. During this time significant precipitation had taken place. The remaining 55 ml of acetonitrile from the original charge plus 30 ml to compensate for the extra DMF were added to the reactor and it was stirred for another 20 hours. Mother liquor concentration at this stage of the process was found to be 45% higher than the typical value for a large-scale crystallization at 0.5 equivalents of HCl. 70 ml of acetonitrile were added to the slurry and it was stirred for another 4 hours. The slurry was then discharged on a 350 ml fine frit sintered glass funnel in 200 ml aliquots. Filtration was extremely fast. The cake was rinsed with 80 ml of acetonitrile and air dried for one and a half hours. It weighed 38.10 grams. The solids were placed in a vacuum oven at 50° C. and 28 inches Hg vacuum for 24 hours. Oven dried solids weighed 36.75 grams. This represented approximately 78% recovery on weight basis and 56% on molar basis. Concentration analysis on the mother liquor samples before the third acetonitrile charge and 4 hours after it, indicated a net reduction of 15% in the concentration of S-[2-[(1-Iminoethyl)amino]ethyl]-2-methyl-L-cysteine in solution. Chloride ion analysis on the filtrate helped verify that HCl equivalent at the onset was 0.73 with 0.23 equivalents attending S-[2-[(1-Iminoethyl)amino]ethyl]-2-methyl-L-cysteine.

Overall shape of the crystals seemed similar to that seen in the preceding experiments, however the bulk density of the powder seemed slightly lower. Table 1 summarizes analytical data on the product from this example.

TABLE 1

Solid state characterization data for Examples 20-22

| Example | C | H | N | S | Cl | Tm | ΔH fus | DMF NMR | Maleic acid NMR |
| --- | --- | --- | --- | --- | --- | --- | --- | --- | --- |
| Theoretical | 40.64 | 6.65 | 14.22 | 10.85 | 6.00 | N/A | N/A | 0.000 | 0.500 |
| 20 | 40.29 | 6.53 | 14.03 | 10.79 | 6.06 | 193.91 | 140.18 | 0.019 | 0.525 |
| 21 | 40.41 | 6.77 | 14.31 | 10.86 | 6.11 | 199.17 | N/A | 0.027 | 0.490 |
| 22 | 40.42 | 6.87 | 14.26 | 10.77 | 6.19 | 199.50 | 130.48 | N/A | N/A |

Example 23

The primary objective of Example 23 was to understand and establish appropriate primary crystallization conditions for the formation of in-situ seeds used as substrate for the orderly packed agglomerates and to reduce the total crystallization time. Acetonitrile was increased by 10% on the amounts used in Examples 19 and 20 and no seeding was performed upon the completion of acetonitrile charge.

15.00 grams of the primary DMF solution of S-[2-[(1-Iminoethyl)amino]ethyl]-2-methyl-L-cysteine, 233.3 mg of maleic acid and 413 microliters of de-ionized water were added to a 50 ml Erlenmeyer flask and stirred to affect a clear solution before being added to a 50 ml jacketed reactor. The reactor was stirred at 153 rpm. 18.2 ml of acetonitrile (from a total of 27.7 ml) were added to the solution in 1.3 ml aliquots over thirty-nine minutes. With the addition of this amount of acetonitrile, needle-like crystals (shape and crystallinity verified by polarized light microscopy) were observed in the reactor. The remaining 9.5 ml of acetonitrile were added in 1.5 ml aliquots over three minutes. Sixty minutes after the addition of 27.7 ml of acetonitrile, another 2.77 ml of acetonitrile were added (this representing the extra 10% on the amounts used in Examples 19 and 20). Agitation was increased to 254 rpm for two hours and then reduced back to 150 rpm. The system was stirred for a total of 24 hours and then the slurry was discharged onto a 30 ml fine frit sintered glass funnel.

Figure 9A:
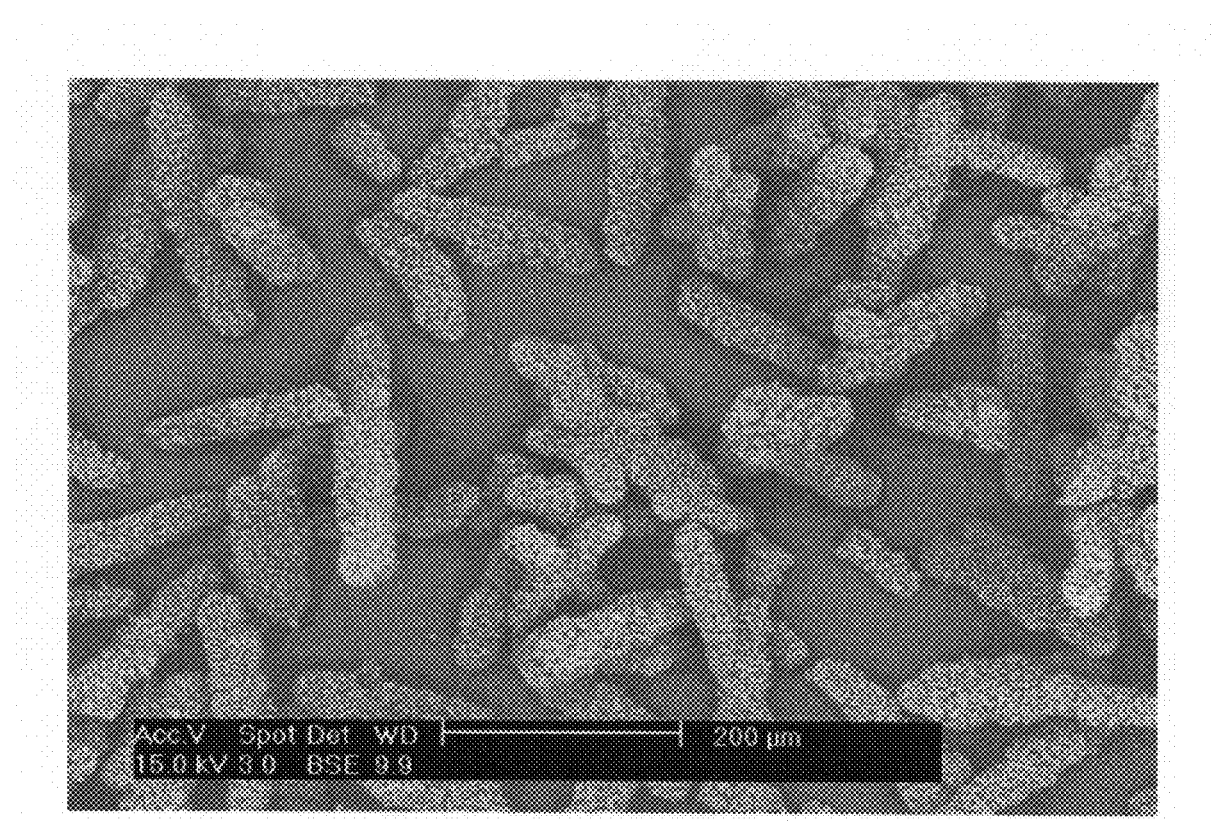
Figure 9B:
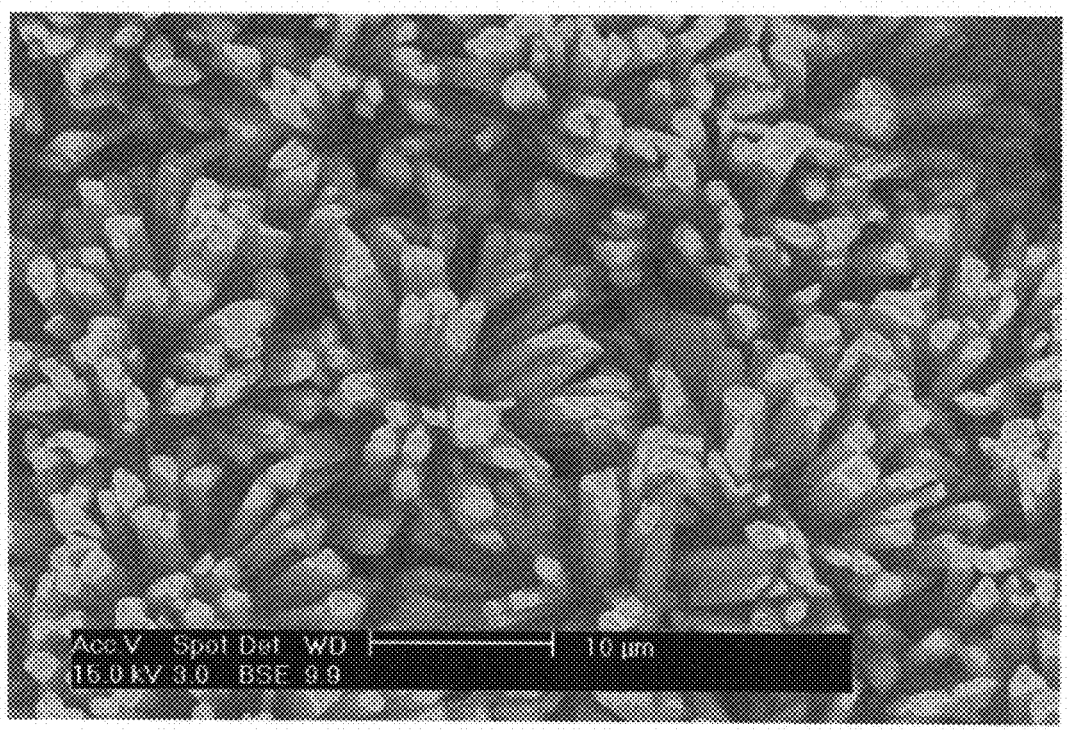
FIG. 9B shows the generally ordered crystals.

Filtration was fast. The cake was rinsed twice with 6 ml of acetonitrile and air dried for one and a half hours. The solids weighed 1.05 grams. The crystals had most of the major features of the orderly packed agglomerates when analyzed by scanning electron microscopy but the overall shape seemed cylindrical (FIG. 9) as opposed to the spherical shape seen in Examples 20, 21 and 22. This difference was attributed to the shape of the seed crystals acting as substrate crystals, which for this example were needle-like.

Example 24

The primary objective of Example 24 was to perform Example 23 at large scale in a 50-liter reactor.

9.5 kg of the secondary DMF solution of S-[2-[(1-Iminoethyl)amino]ethyl]-2-methyl-L-cysteine solution were added to a 50 liter jacketed reactor. The reactor was stirred at 125 rpm. 11.04 liters of acetonitrile (from a total of 18.45 liters) were added to the solution in 840 ml aliquots over thirty-six minutes. During the addition of this amount of acetonitrile, needle-like crystals (shape and crystallinity verified by polarized light microscopy) were observed in the reactor. 4.97 liter of acetonitrile were added in 1.65 liter aliquots over nine minutes and the remaining 2.42 liter was added after forty-eight minutes from the start of the original acetonitrile charge. The system was stirred for a total of six hours and then the slurry was discharged on the filter.

Filtration was fast and only took eight minutes. The cake was rinsed twice with 2.0 kg of acetonitrile and air dried for twenty-four hours. The solids weighed 1.08 kg. The crystals had most of the major features of the orderly packed agglomerates when analyzed by scanning electron microscopy but the overall shape seemed similar to that obtained in Example 23 and unlike the spherical shape seen in Examples 20, 21 and 22. This difference was attributed to the shape of the substrate crystals, which for this example was needle-like.

Example 25

The primary objective of Example 25 was to increase the amount of acetonitrile by 20% on the amounts used in examples 20 and 21 and to study the possibility of eliminating both external and in-situ seeding with S-[2-[(1-Iminoethyl)amino]ethyl]-2-methyl-L-cysteine maleate hydrochloride prior to, during or just after phase separation. 25.01 grams of the primary DMF solution of S-[2-[(1-Iminoethyl)amino]ethyl]-2-methyl-L-cysteine solution and 687 mg of de-ionized water were added to a 125 ml jacketed reactor. 346 mg of maleic acid were added to the reactor and the system was stirred at 173 rpm to affect a clear solution. 56 ml of acetonitrile were added to the solution in 3 ml aliquots over sixty minutes. The solution became very turbid with the addition of the last aliquot of acetonitrile, however, most of the turbidity subsided within fifteen minutes, leaving behind thin oily coating on the walls of the reactor. The reactor was heated to 55° C. (temperature of the jacket) in order to determine if the oily coating could be dissolved. The operation did not succeed and the reactor was cooled back to room temperature. The system was stirred for 48 hours and then the slurry was discharged onto a 150 ml fine frit sintered glass funnel.

Filtration was fast. The cake was rinsed with 10 ml of acetonitrile and air dried for one and a half hours. The solids weighed 1.57 grams and had all the major features of the orderly packed agglomerates when analyzed by scanning electron microscopy.

Some solids were observed to be plastered on the walls of the reactor. This scale was removed by slurrying in 25 ml of acetonitrile and then filtered on 150 ml fine frit sintered glass funnel. The solids were air dried for 1 hour and they weighed 1.01 grams. These solids had shape features similar to those of randomly packed agglomerates.

Example 26

The objective of Example 26 was to determine if orderly packed agglomerates could be converted into small crystals that would then compact as randomly packed agglomerates.

200 mg of orderly packed agglomerates of S-[2-[(1-Iminoethyl)amino]ethyl]-2-methyl-L-cysteine maleate hydrochloride crystals made in Example 20, were added to an 8 ml vial. 3.95 grams of the filtrate from Example 23 and a magnetic bead was added to the vial and the resulting slurry was stirred through a magnetic plate at maximum speed for 4 days. Slurry samples were withdrawn each day for photo-microscopy to check if the orderly packed agglomerates were grinding in the very narrow gap between the stirring magnetic bead and the bottom of the vial.

Photo-microscopy analysis indicated that at least 72 hours (or 3 days) were necessary to completely grind the orderly packed crystals. These ground crystals compacted into randomly packed agglomerates upon filtration.

Alternative Solvent Systems

Example 27

Methanol/Acetone Crystallization

Methanol is one of the few organic solvents in which S-[2-[(1-Iminoethyl)amino]ethyl]-2-methyl-L-cysteine maleate hydrochloride crystals exhibit moderate solubility (6.2 wt %). Additionally, the presence of excess maleic acid dramatically increases the solubility. S-[2-[(1-Iminoethyl)amino]ethyl]-2-methyl-L-cysteine maleate hydrochloride crystals were found to readily dissolve in as little as 4 g methanol per gram S-[2-[(1-Iminoethyl)amino]ethyl]-2-methyl-L-cysteine maleate hydrochloride in the presence of 1.5 eq. excess maleic acid. Making only minor adjustments to the demonstrated DMF/acetonitrile process, the methanol/acetone crystallization process described below was developed and demonstrated at the 1 L scale.

Maleic acid (23.57 g-1.5 Eq.) was charged to a 500 mL roundbottom flask. Methanol (160 g-4 g per gram) was added and the flask was stirred to form a clear solution. S-[2-[(1-Iminoethyl)amino]ethyl]-2-methyl-L-cysteine maleate hydrochloride (40.00 g) was then charged to the round bottom flask and dissolved to form a clear solution. This solution was charged to a jacketed 1 L reactor operating at room temperature. Agitation was set to 225 rpm.

Acetone (544 g-17 mL per gram) was weighed out, and a peristaltic pump was calibrated to deliver approximately 9 mL per minute. Fifteen minutes into the acetone addition, the solution turned slightly hazy but clarified upon increasing agitation. After 1 hour 20 minutes of addition (44.68 g of acetone remaining to be added) the crystallization mixture was distinctly turbid. The acetone addition was stopped, and 400 mg of seeds were added. Agitation was set to 240 rpm and stirred overnight. The crystallization mixture was a thick slurry after 17 hours. Solids were filtered and washed twice with acetone and dried on the filter. Yield was 74.8%.

Example 28

Butanol/Acetone Crystallization

1-Butanol was selected as the best solvent to explore the possibility of utilizing a high boiling solvent that can easily be exchanged with water from the upstream aqueous chromatography purification step. While S-[2-[(1-Iminoethyl)amino]ethyl]-2-methyl-L-cysteine maleate hydrochloride does not exhibit high solubility in 1-butanol (0.05 wt %), the addition of excess maleic acid greatly increases its solubility. This process was again designed to be very similar to the DMF/acetonitrile process. Following is a description of the initial process run at the 1 L scale.

S-[2-[(1-Iminoethyl)amino]ethyl]-2-methyl-L-cysteine maleate hydrochloride (38 g), DI water (200 mL), l-Butanol (500 mL), and maleic acid (29.46 g-1.5 eq.) were added to a jacketed 1 L reactor. The mixture was stirred to form a clear solution. This solution was distilled under vacuum (135 torr) and temperature of 53-67 C to 20 mL. 1-Butanol (250 mL) was charged and distillation was continued at 135 torr and 70 C until the volume was reduced to 20 mL. The temperature was adjusted to 50 C. DI Water (2.5 mL) and 1-butanol (475 mL) were charged. S-[2-[(1-Iminoethyl)amino]ethyl]-2-methyl-L-cysteine maleate hydrochloride crystal seeds (1.5 g) were added and washed into the reactor with 1-butanol (25 mL). Acetone (300 mL) was added to the crystallization mixture over 3 hours via syringe pump. One hour after the acetone addition was complete, the crystallization mixture was cooled to 10 C over 10 hours. The crystallization mixture was filtered for 14 hours after acetone addition was complete. The crystallization mixture filtered very easily and no cake cracking was observed. An acetone wash (300 mL) was charged to the reactor and rinsed onto the cake. Solids were dried in a vacuum oven at 50 C, 24 inches Hg overnight. The product mass was 40.45 g, representing a yield of 78%.

DSC analysis showed that the solid state form of both products was crystalline S-[2-[(1-Iminoethyl)amino]ethyl]-2-methyl-L-cysteine maleate hydrochloride. The solvent content of each product, after drying overnight under vacuum at 50 C is shown in Table 2.

TABLE 2

| | Residual Solvent Content | | |
|---|---|---|---|
| Example No. | Methanol | Butanol | Acetone |
| 27 (methanol/acetone) | 0.64% | N/A | 1.37% |
| 28 (butanol/acetone) | N/A | 0.39% | 1.10% |

The 1-butanol/acetone system may be preferable, as both are Class III solvents.

The penultimate step is SMB chromatography purification that is most easily performed in an aqueous solution. Solvent exchanging from water into 1-butanol can be easily achieved, but complete removal of water from a methanol system would not be possible. This also favors the 1-butanol/acetone system over the methanol/acetone system.

Process Development

Similar to the DMF/acetonitrile crystallization, the 1-butanol/acetone crystallization has several parameters that can affect the crystallization. Intrinsic parameters include: 1) temperature, 2) hydrochloric acid content, 3) maleic acid content, 4) water content, 5) compound loading, and 6) acetone amount. Extrinsic parameters include: 1) seeding, 2) reactor geometry, 3) acetone addition protocol and 4) mixing. Each of these parameters is discussed in greater detail below.

Intrinsic Parameters

1. Temperature

Example 29

Maleic acid (0.59 g-1.5 eq) was weighed out in a 50 mL roundbottom flask. 1-butanol (8 g) was charged and the mixture was stirred to form a clear solution. S-[2-[(1-Iminoethyl)amino]ethyl]-2-methyl-L-cysteine maleate hydrochloride (1.00 g) and water (1000 uL) were charged and the mixture was stirred to form a clear colorless solution. The solution was rotary evaporated at 50 C. 1-butanol (6 g) was charged and rotary evaporation continued. l-Butanol (8 g) was added to make a flowable solution. 1-Butanol (2.89 g) and water (l 30 uL) were charged to take the solution to the desired initial conditions: 0.5 Eq. HCL, 2.0 Eq. maleic acid, 14 volumes 1-butanol/Kg S-[2-[(1-Iminoethyl)amino]ethyl]-2-methyl-L-cysteine maleate hydrochloride, KF=1.5%. Acetone (6 mL) was charged dropwise. Nucleation was not observed during the acetone charge. S-[2-[(1-Iminoethyl)amino] ethyl]-2-methyl-L-cysteine maleate hydrochloride crystal seeds (10 mg) were charged followed by an addition amount of acetone (0.5 mL). The crystallization mixture was stirred at room temperature and appeared to be a thick slurry after several hours. The crystallization appeared to behave in a manner very similar to the DMF/acetonitrile crystallization. The slurry was filtered on a 15 mL fine frit sintered glass funnel. The cake was washed twice with 15 mL acetone and pulled dry.

Microanalytical, DSC, and PXRD show the solids to be crystalline S-[2-[(1-Iminoethyl)amino]ethyl]-2-methyl-L-cysteine maleate hydrochloride. Microanalytical and DSC data are summarized in Table 3.

TABLE 3

Isothermal room temperature crystallization data

| Example | Description | Microanalytical | | | | DSC | |
|---|---|---|---|---|---|---|---|
| | | C | H | N | Cl | Temp (C.) | Enthalpy |
| 29 | Room Temp. | 40.46 | 13.90 | 6.81 | 5.85 | 200.15 | 148.1 J/g |
| | Theory | 40.64 | 14.22 | 6.65 | 6.00 | | |

The 1-butanol/acetone crystallization proceeded at room temperature as expected with no nucleation occurring prior to the charge of seeds. The product was crystalline S-[2-[(1-Iminoethyl)amino]ethyl]-2-methyl-L-cysteine maleate hydrochloride.

2. Hydrochloric Acid

HCl plays a role in the behavior of the crystallization. It is desired to have a stoichiometric amount (0.5 eq) HCl in the system. Below this target amount could result in a reduced yield, as HCl becomes the limiting reagent, or result in a mixture of S-[2-[(1-Iminoethyl)amino]ethyl]-2-methyl-L-cysteine maleate hydrochloride and the 1:1 maleate salt (S-[2-[(1-Iminoethyl)amino]ethyl]-2-methyl-L-cysteine maleate, Form II). Excess HCl in the system would likely result in reduced yields due to increased solubility and solids with poor physical properties.

3. Maleic Acid

Example 30

It is known that an excess of maleic acid is required based on work done with the DMF/acetonitrile crystallization, and the target amount for the initial experiment was 2.0 equivalents. A crystallization mixture with 1.75 equivalents of maleic acid was brought to the initial conditions: 0.5 eq. HCl, 1.75 Eq. maleic acid, 14 volumes 1-BuOH/g S-[2-[(1-Iminoethyl)amino]ethyl]-2-methyl-L-cysteine maleate hydrochloride, 1.5% KF.

Upon cold storage overnight of this solution, solids were observed to precipitate out. It appears therefore that having only 1.75 equivalents of maleic results in an unstable supersaturated solution that can precipitate out readily.

Three side-by-side crystallizations (Examples 30A, 30B and 30° C.) were run with 2.0, 2.25, and 2.50 eq. Maleic, receptively, to evaluate the effect on the crystallization. Maleic acid (1.78 g-1.5 eq) was charged to a 100 mL round bottom flask. I-Butanol (34.0 g-14 vols) was charged and stirred to dissolve. S-[2-[(1-Iminoethyl)amino]ethyl]-2-methyl-L-cysteine maleate hydrochloride (3.00 g) was charged to the solution. Water was charged (3200 uL) and the mixture was stirred to form a clear solution. The solution was rotary evaporated at 55 C under vacuum. I-Butanol (24 g) was charged back to the mixture and rotary evaporation was continued until KF was 1.00%. Butanol (23.29 g) and water (0.434 g) was added to take the solution to 14 volumes 1-butanol/S-[2-[(1-Iminoethyl)amino]ethyl]-2-methyl-L-cysteine maleate hydrochloride and KF of 1.5%. The solution was divided into 3 portions (12.9 g each) and labeled "A", "B", and "C". 98 mg maleic acid (0.25 eq) was charged to flask B and 197 mg maleic acid (0.5 eq) charged to flask C and each was stirred to form a clear solution.

Acetone (6 mL) was charged to each flask dropwise in 1 mL aliquots over 35 minutes. Each experiment was observed to nucleate during the acetone charge; the most solids were observed with the low maleic acid content (2.0 eq.) and the least with the highest maleic acid content (2.50 eq.). At the end of the acetone addition, 10 mg seeds were charged to each flask and the experiments were held at room temperature over the weekend. Each experiment was filtered on a 15 mL fine frit sintered glass funnel and the cake was washed twice with 15 mL acetone. The cakes were pulled dry on the filter.

Microanalytical and DSC data on the isolated solids from each experiment are summarized in Table 3. In all three experiments, microanalytical data match those predicted by theory for S-[2-[(1-Iminoethyl)amino]ethyl]-2-methyl-L-cysteine maleate hydrochloride. DSC results for all lots also show a large endothermic event near 200 C, corresponding to the melting point of S-[2-[(1-Iminoethyl)amino]ethyl]-2-methyl-L-cysteine maleate hydrochloride. In Example 30A, there is a very small event at 54 C that could correspond to a small amount of S-[2-[(1-Iminoethyl)amino]ethyl]-2-methyl-L-cysteine maleate, form II. This is very likely due to the considerable amount of uncontrolled nucleation that occurred during the acetone charge in this particular Example. Since nucleation occurred during the acetone charge even in the presence of 2.50 eq. maleic acid, albeit to a lesser degree, it appears that the acetone addition rate was far too fast. The small amount of S-[2-[(1-Iminoethyl)amino]ethyl]-2-methyl-L-cysteine maleate, form II formed in the presence of only 2.0 eq. maleic acid is therefore not likely due to low maleic acid levels directly, but could likely be avoided with a slower acetone addition rate.

TABLE 4

Microanalytical and DSC Data - Varying Maleic Acid

| Example | Description | Microanalytical | | | | DSC | |
|---|---|---|---|---|---|---|---|
| | | C | H | N | Cl | Temp (C.) | Enthalpy |
| 30A | 2.0 Eq. Maleic | 40.27 | 13.95 | 6.64 | 5.93 | 54.28 199.52 | 7.3 J/g 156.9 J/g |
| 30B | 2.25 Eq. Maleic | 40.50 | 13.98 | 6.70 | 5.91 | 201.11 | 148.4 J/g |
| 30C | 2.50 Eq. Maleic | 40.47 | 13.91 | 6.61 | 5.84 | 199.75 | 159.4 J/g |
| | Theory | 40.64 | 14.22 | 6.65 | 6.00 | | |

Analysis of the mother liquor from each experiment summarized in Table 3 showed that, as expected, concentration of S-[2-[(1-Iminoethyl)amino]ethyl]-2-methyl-L-cysteine increased with increasing maleic acid. Lower maleic acid content in the crystallization system, therefore, is expected to increase yield.

TABLE 5

Mother Liquor Analysis

| Example | Description | Wt % S-[2-[(1-Iminoethyl)amino]ethyl]-2-methyl-L-cysteine |
|---|---|---|
| 30A | 2.0 Eq. Maleic Acid | 0.84% |
| 30B | 2.25 Eq. Maleic Acid | 0.90% |
| 30C | 2.50 Eq. Maleic Acid | 1.09% |

Based on this Example, maleic acid content in the range of 2.0-2.5 will result in formation of S-[2-[(1-Iminoethyl)

amino]ethyl]-2-methyl-L-cysteine maleate hydrochloride, provided the addition rate of acetone does not cause considerable nucleation during the charge. Maleic acid as low as 1.75 eq. may result in an unstable supersaturated solution that could readily crash out in the event of extended hold times. It is desirable, therefore, to target the maleic acid range of 2.0 to 2.25 eq. in the crystallization system.

4. Water Content

At water levels at or below 4% at 25 C, S-[2-[(1-Iminoethyl)amino]ethyl]-2-methyl-L-cysteine maleate hydrochloride is the stable form. Above 4%, mixtures of S-[2-[(1-Iminoethyl)amino]ethyl]-2-methyl-L-cysteine maleate hydrochloride and S-[2-[(1-Iminoethyl)amino]ethyl]-2-methyl-L-cysteine maleate, Form II are observed. It is preferable, therefore to target the water content of the system to be below 4% for formation of crystalline S-[2-[(1-Iminoethyl)amino]ethyl]-2-methyl-L-cysteine maleate hydrochloride

5. Compound Loading

Operating at 14 volumes 1-butanol seems to result in the most controlled crystallization, and the increased volume does not appear to adversely affect yield. It is preferable, therefore, to utilize 14 volumes of 1-butanol per g of S-[2-[(1-Iminoethyl)amino]ethyl]-2-methyl-L-cysteine maleate hydrochloride.

6. Acetone Amount

Typically, 6 volumes of acetone per gram of S-[2-[(1-Iminoethyl)amino]ethyl]-2-methyl-L-cysteine maleate hydrochloride have been used. At the end of this addition, one can observe the bursts of white solids coming out of solution with the addition of each drop of acetone. The solids characteristically dissipate, but the solution is often slightly turbid upon addition of the complete six volumes. These observations suggest that the system is highly supersaturated at this point and that adding significantly more than 6 volumes of acetone could result in over-stressing the phase separation. Adding significantly less acetone, alternatively, may not allow the system to reach phase separation. This could not only jeopardize the spherical agglomerate morphology but also negatively impact the yield.

Extrinsic Parameters

1. Seeding

Briefly, the addition of seeds at the time of phase separation may assist in controlling the crystallization. Having solids present in the bulk at the time of phase separation provides a substrate upon which the dispersed phase can deposit and crystallize into agglomerates. Controlling the size and shape of the substrate through controlled seed addition versus nucleation in the bulk may also be important for controlling the overall shape of the agglomerate. Throughout the development of the process, the amount of seed added to the 1-butanol/acetone system has varied from 1-3% of the total S-[2-[(1-Iminoethyl)amino]ethyl]-2-methyl-L-cysteine maleate hydrochloride in the batch. No dramatic difference in the behavior of the crystallization was observed.

In the initial 1-butanol/acetone process used, seeds (3%) were charged prior to the acetone addition. In order to ensure a monodisperse particle size distribution, it is preferable to charge seeds as close to the time of phase separation as possible. Charging seeds prior to initiating the acetone addition may cause nucleation at different times during the charge, resulting in a multi-modal distribution.

A protocol similar to that used in the DMF/acetonitrile crystallization may be preferable in the 1-butanol/acetone crystallization. After the bulk (~90%) of the solvent charge, a seed slurry of approximately half of the remaining 10% would be charged. The remaining solvent would be used as a rinse of the seed vessel and charge lines.

2. Reactor Characteristics

Based upon experience with the DMF/acetonitrile system, reactor geometry also may affect the performance of the crystallization, most directly in terms of the yield. It is not favorable to perform the crystallization in a crystallizer with a large aspect ratio and a large surface to volume ratio, such as in a small cylindrical vial. At the time of phase separation, the dispersed phase may be deposited on the walls instead of on the seed crystals. In the extreme case, small-scale crystallizations conducted without seeding in narrow vials have resulted in crystallization entirely on the walls with virtually no solids in the bulk. As the 1-butanol/acetone crystallization is also a phase separating system, a reactor with a relatively small aspect ratio and small surface to volume ratio is expected to be optimal.

3. Acetone Addition

The acetone addition protocol has varied from as little as 35 minutes to as long as 3 hours and 45 minutes. As noted in section 4.1.3, addition of acetone too quickly can result in the premature nucleation of sticky solids in the bulk, which can lead to a mixture of salts in the final product. Charging acetone over 3 hour 45 minutes showed virtually no advantage over a 2 hour or 1 hour charge time. At the end of the addition, the solution was turbid in all cases and all crystallizations proceeded as expected, resulting in high quality S-[2-[(1-Iminoethyl)amino]ethyl]-2-methyl-L-cysteine maleate hydrochloride. It appears, therefore, that while charging acetone too quickly can result in shortened induction time and the premature nucleation of solids during the acetone addition, there is not an obvious limit for the maximum addition time. A target addition time of two hours may be preferred, as it is in the middle of the range found to be acceptable.

4. Mixing

Mixing is an important parameter with respect to liquid-liquid phase separation crystallizations. Agitation should be sufficient such that the dense agglomerates formed do not settle in a "deadzone" underneath the agitator. At large scale, it may be useful to blow nitrogen up gently through the bottom valve to minimize the deadzone.

It appears that the spherical agglomerates are fairly robust and not easily broken up during extended agitation periods, and the agglomerates appear to be intact after 11 days of stirring.

In the event that chromatography is incorporated into the synthetic process of S-[2-[(1-Iminoethyl)amino]ethyl]-2-methyl-L-cysteine maleate hydrochloride, it is recommended that the chromatographed product be well characterized before proceeding with the final crystallization. In preparation for chromatography, S-[2-[(1-Iminoethyl)amino]ethyl]-2-methyl-L-cysteine maleate hydrochloride crude product is dissolved in water with a slight excess (~0.2 eq.) of maleic acid. The purified aqueous solution is the starting material for the final 1-butanol/acetone crystallization.

It is recommended that the purified aqueous solution be well characterized in terms of concentration, maleic acid content, as well as HCl content prior to use in the 1-butanol/ acetone crystallization. It is unknown if portions of HCl may be removed in chromatography. In previous work, chloride ion concentration was measured by ion chromatography. If the chloride content is significantly below 0.5 eq (<0.45), it is recommended to add HCl to target the desired value.

The chromatography is run with only a slight excess of maleic acid. Maleic acid therefore may be added to the purified solution to achieve the target 2.0 equivalents. Additionally, the concentration S-[2-[(1-Iminoethyl)amino]ethyl]-2-methyl-L-cysteine (freebase) should be accurately quantified as the basis of the acid additions. Both the maleic acid and S-[2-[(1-Iminoethyl)amino]ethyl]-2-methyl-L-cysteine free base concentrations have been quantitated using HPLC.

If chromatography is removed from the synthesis, the solvent exchange to achieve the appropriate initial conditions can be simplified by using 1-butanol as the primary dissolution solvent and adding just enough water (~8% by KF) to obtain a clear colorless solution. This solution is then distilled for only a short time to achieve a KF of less than 1.5%.

Powder Characteristics of Spherical Orderly Packed Agglomerates of S-[2-[(1-Iminoethyl)Amino]Ethyl]-2-Methyl-L-Cysteine Maleate Hydrochloride Crystals Orderly packed agglomerates of S-[2-[(1-Iminoethyl)amino]ethyl]-2-methyl-L-cysteine maleate hydrochloride crystals made in Example 20 were studied to determine its powder characteristics that are relevant to the development of a pharmaceutical composition with S-[2-[(1-Iminoethyl)amino]ethyl]-2-methyl-L-cysteine maleate hydrochloride together with a pharmaceutically acceptable carrier. Before testing, the solids were passed through 80-mesh screen corresponding to 177 micrometer opening in order to fragment some very large loose aggregates of the orderly packed agglomerates. The properties tested included powder flow characteristics, powder particle size distribution, powder bulk and tapped density and powder compressibility and compaction.

Powder flow was evaluated using an aperture flow tester, measured as the smallest opening at which the powder freely flows through. The powder flow test was repeatedly successful through a 6-mm aperture opening. A powder flow of 6-mm is considered good for formulation development of S-[2-[(1-Iminoethyl)amino]ethyl]-2-methyl-L-cysteine maleate hydrochloride crystals. Successful repetition of flow through a narrower 4-mm opening was, however, dependent on how the powder was introduced to the tester. The calculated compressibility index of 17.8% also indicated good to fair flow characteristics for these orderly packed agglomerates of S-[2-[(1-Iminoethyl)amino]ethyl]-2-methyl-L-cysteine maleate hydrochloride crystals.

Figure 12:
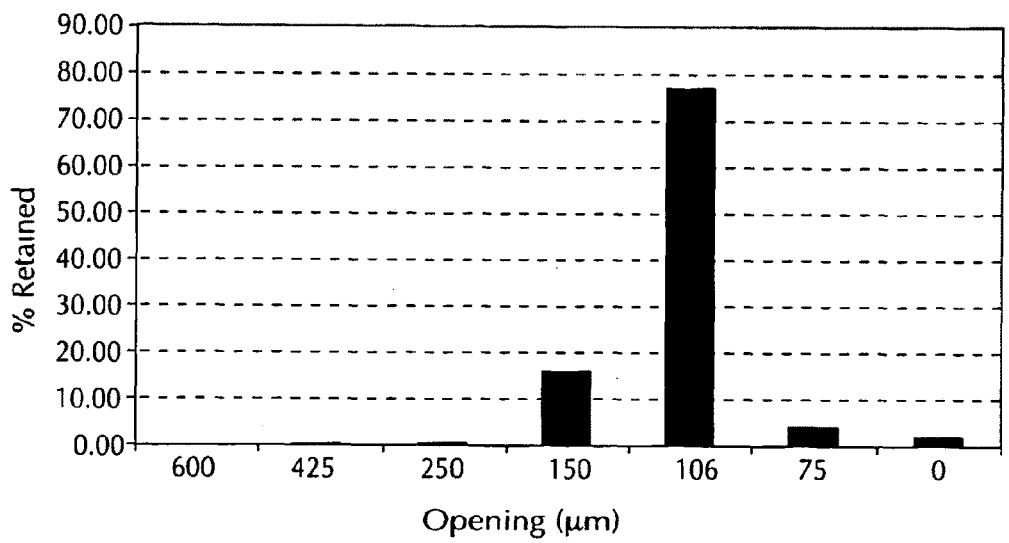
FIG. 12 shows a graph of particle size distribution of orderly packed agglomerates of S-[2-[(1-Iminoethyl)amino]ethyl]-2-methyl-L-cysteine maleate hydrochloride crystals.

Particle size distribution of the powder was measured using sieve analysis. The mean particle size distribution was calculated using the geometric mean method. The particle size distribution data is presented in FIG. 12. These orderly packed agglomerates displayed a mean particle size of 134 micrometers (referred to from here on as μm). Only 1.63% of material was considered as fines, less than 75-μm, with more than 90% within 105-250-μm. More than 75% of the material was within 105-150-μm. The tight range in the powder particle size distribution for orderly packed agglomerates is between 100 and 200-μm, which is highly desirable for the development of a pharmaceutical composition with S-[2-[(1-Iminoethyl)amino]ethyl]-2-methyl-L-cysteine maleate hydrochloride together with a pharmaceutically acceptable carrier.

Bulk powder density was evaluated as the mass of material within a 50-ml graduated cylinder. Tapped powder density was calculated at the equilibrium point, where addition tapping did not alter the powder volume. Orderly packed agglomerates exhibited a bulk powder density of 0.41-g/ml, with a tapped density of 0.50-g/ml.

Figure 13:
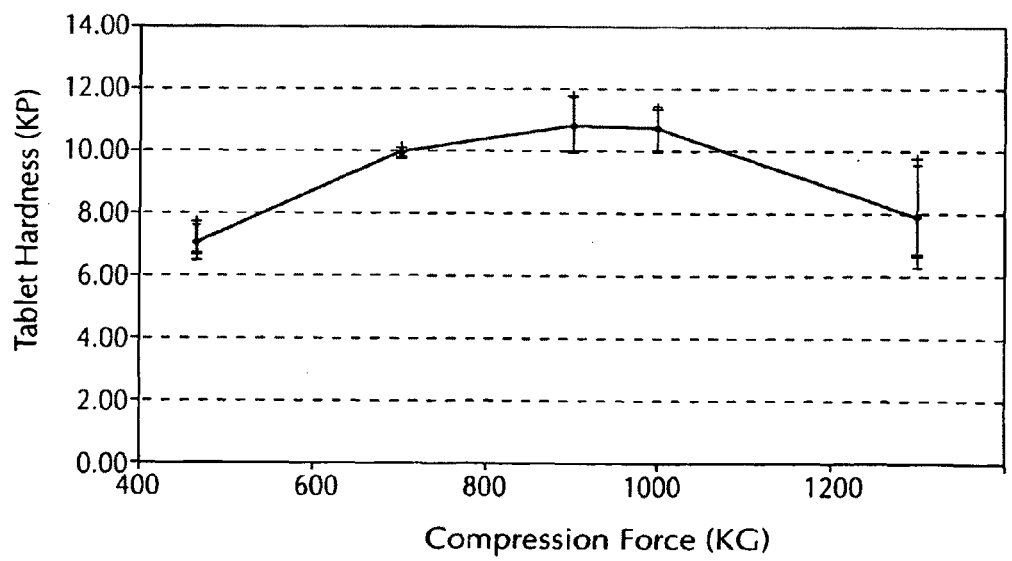
FIG. 13 is a graph plotting tablet hardness as a function of compression force.
Figure 14:
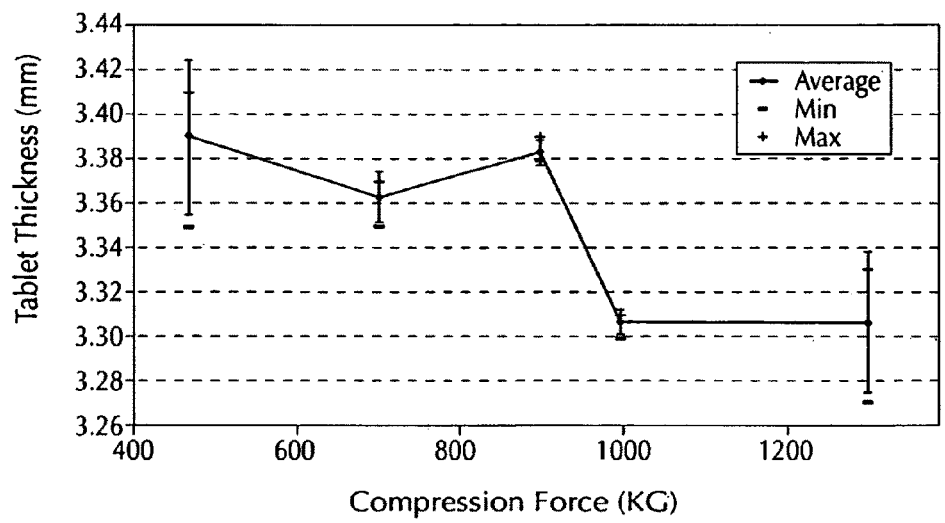
FIG. 14 is a graph plotting tablet thickness as a function of compression force.
Figure 15:
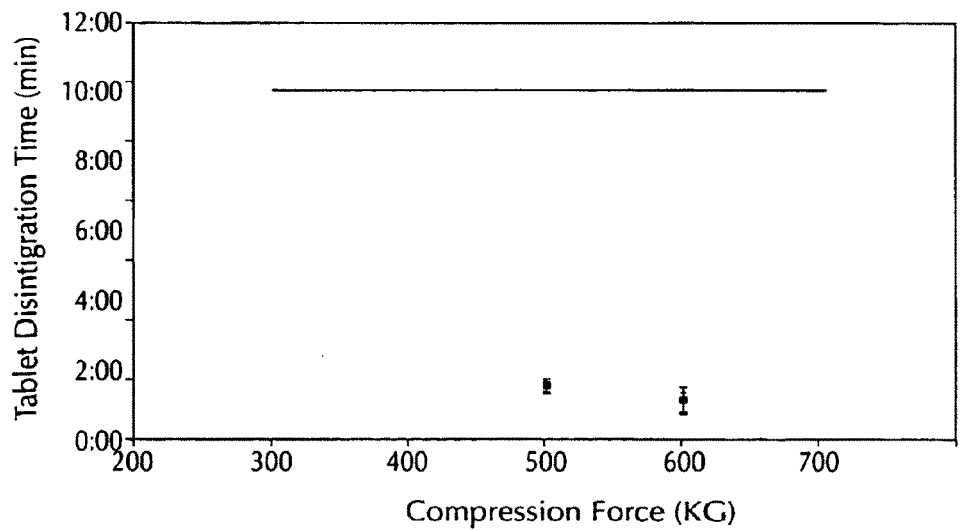
FIG. 15 is a graphical representation of tablet disintegration time.

The powder was evaluated for direct compression without any excipients. Compacts of 100-mg in weight were manufactured using an 8/32 inch (6.35-mm) round concave tooling. Tablets were compressed at various compression forces and evaluated for strength, thickness and disintegration. The direct compression profile of orderly packed agglomerates of S-[2-[(1-Iminoethyl)amino]ethyl]-2-methyl-L-cysteine maleate hydrochloride crystals is presented in FIG. 13 The orderly packed agglomerates of S-[2-[(1-Iminoethyl)amino]ethyl]-2-methyl-L-cysteine maleate hydrochloride crystals displays good compressibility profile, without use of excipients. Relatively strong small tablets (8/32 inch), as hard as 11-kP, are possible with compression force between 900 and 1000 kg. Tablet strength reaches an apparent maximum between 900 and 1000 kg compression force. Minor adhesion to the punch and die walls were observed during compression experiments. However, the sticking was considered to be a minor problem and could easily be resolved by using an appropriate lubricant. The effect of tablet thickness as a function of compression force is presented in FIG. 14. Tablet disintegration times were also evaluated for compacts of orderly packed agglomerates of S-[2-[(1-Iminoethyl)amino]ethyl]-2-methyl-L-cysteine maleate hydrochloride crystals. Three tablets were compressed with compression forces between 500 and 600, corresponding to 8 kP tablet hardness for this material. All tablets displayed rapid disintegration times of less than 2 minutes and well below the target of 10 minutes (See FIG. 15).

In summary, orderly packed agglomerates of S-[2-[(1-Iminoethyl)amino]ethyl]-2-methyl-L-cysteine maleate hydrochloride crystals show highly desirable properties for the development of a pharmaceutical composition, such as tablets, with S-[2-[(1-Iminoethyl)amino]ethyl]-2-methyl-L-cysteine maleate hydrochloride together with a pharmaceutically acceptable carrier.

Pharmaceutical Compositions

Also embraced within this invention is a class of pharmaceutical compositions comprising crystalline S-[2-[(1-Iminoethyl)amino]ethyl]-2-methyl-L-cysteine maleate hydrochloride in association with one or more non-toxic, pharmaceutically-acceptable carriers and/or diluents and/or adjuvants (collectively referred to herein as "carrier" materials) and, if desired, other active ingredients. The crystalline of S-[2-[(1-Iminoethyl)amino]ethyl]-2-methyl-L-cysteine maleate hydrochloride of the present invention may be administered by any suitable route, preferably in the form of a pharmaceutical composition adapted to such a route, and in a dose effective for the treatment intended. The active S-[2-[(1-Iminoethyl)amino]ethyl]-2-methyl-L-cysteine maleate hydrochloride and compositions may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compound and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

Crystalline S-[2-[(1-Iminoethyl)amino]ethyl]-2-methyl-L-cysteine maleate hydrochloride can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0-5 to 20%, advantageously 0.5 to 100% and particularly about 1.5% w/w.

For therapeutic purposes, S-[2-[(1-Iminoethyl)amino] ethyl]-2-methyl-L-cysteine maleate hydrochloride is ordinarily combined with one or more adjuvants appropriate to the indicated route of administration. If administered per os, the compound may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The crystalline S-[2-[(1-Iminoethyl)amino]ethyl]-2-methyl-L-cysteine, maleate hydrochloride may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A method of making generally orderly packed agglomerate crystalline S-[2-[(1-Iminoethyl)amino]ethyl]-2-methyl-L-cysteine maleate hydrochloride utilizing a crystallization procedure comprising adding an anti-solvent to a solvent solution in which is dissolved S-[2-[(1-Iminoethyl)amino] ethyl]-2-methyl-L-cysteine maleate hydrochloride, thereby forming a system comprising two phases, and precipitating generally orderly packed agglomerate crystalline S-[2-[(1-Iminoethyl)amino]ethyl]-2-methyl-L-cysteine maleate hydrochloride, wherein the anti-solvent comprises acetonitrile or acetone and the solvent comprises 1-butanol or N,N-dimethylformamide.

2. The method of claim 1 wherein the anti-solvent is added to the solvent solution in which is dissolved S-[2-[(1-Iminoethyl)amino]ethyl]-2-methyl-L-cysteine maleate hydrochloride, followed by addition of seed crystals to the system.

3. The method of claim 1 wherein the anti-solvent comprises acetone.

4. The method of claim 1 wherein the solvent solution comprises 1-butanol and S-[2-[(1-Iminoethyl)amino]ethyl]-2-methyl-L-cysteine maleate hydrochloride.

5. The method of claim 1 wherein the anti-solvent comprises acetonitrile, and the solvent solution comprises N,N-dimethylformamide and S-[2-[(1-Iminoethyl)amino]ethyl]-2-methyl-L-cysteine maleate hydrochloride.

6. The method of claim 1 wherein the anti-solvent comprises acetone, and the solvent solution comprises 1-butanol and S-[2-[(1-Iminoethyl)amino]ethyl]-2-methyl-L-cysteine maleate hydrochloride.

7. The method of claim 2 wherein no less than about one percent by weight of the total S-[2-[(1-Iminoethyl)amino] ethyl]-2-methyl-L-cysteine maleate hydrochloride in the system is introduced as added seed crystals.

8. The method of claim 1 wherein a sufficient amount of anti-solvent is added to a solvent solution comprising S-[2-[(1-Iminoethyl)amino]ethyl]-2-methyl-L-cysteine maleate hydrochloride in a reaction vessel to form a reaction system, until one of a) turbidity or b) an oily coating on a surface of said reaction vessel is visually apparent, and adding seed crystals to said system.

9. The method of claim 2 wherein the seed crystals are created in-situ by at least one of: reducing the water content of the solvent solution; reducing the amount of maleic acid; or altering the rate of super-saturation generation.

10. The method of claim 1 wherein no seed crystals are added to the system, and the ratio of anti-solvent added to the system exceeds the ratio of solvent solution in which is dissolved S-[2-[(1-Iminoethyl)amino]ethyl]-2-methyl-L-cysteine maleate hydrochloride by about one hundred and ten percent by weight that of the ratio of anti-solvent to solvent used in a system wherein seed crystals are added, to precipitate generally orderly packed agglomerate crystalline S-[2-[(1-Iminoethyl)amino]ethyl]-2-methyl-L-cysteine maleate hydrochloride.

* * * * *